United States Patent [19]
Osborn, III et al.

[11] Patent Number: 6,042,575
[45] Date of Patent: *Mar. 28, 2000

[54] GENERALLY THIN, FLEXIBLE, SANITARY NAPKIN WITH CENTRAL ABSORBENT HUMP

[75] Inventors: Thomas Ward Osborn, III, Cincinnati; Deborah Catherine Schmitz, West Chester, both of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/686,879

[22] Filed: Jul. 26, 1996

Related U.S. Application Data

[62] Division of application No. 08/563,879, Nov. 21, 1995, which is a continuation of application No. 08/007,207, Jan. 22, 1993, which is a continuation-in-part of application No. 07/892,393, May 28, 1992, Pat. No. 5,324,278, application No. 07/934,585, Aug. 24, 1992, Pat. No. 5,281,208, application No. 07/915,286, Jul. 23, 1992, Pat. No. 5,382,245, application No. 07/734,405, Jul. 23, 1991, Pat. No. 5,334,176, application No. 07/944,764, Sep. 14, 1992, abandoned, application No. 08/204,794, Mar. 2, 1991, application No. 08/665,595, Jun. 18, 1996, application No. 07/882,738, May 14, 1992, application No. 07/915,133, Jul. 23, 1992, Pat. No. 5,824,004, application No. 08/166,660, Dec. 13, 1993, application No. 08/268,869, Jun. 30, 1994, Pat. No. 5,849,003, application No. 08/238,191, May 4, 1994, application No. 08/315,315, Sep. 29, 1994, application No. 08/288,656, Aug. 10, 1994, application No. 07/957,575, Oct. 7, 1992, and application No. 07/966,240, Oct. 26, 1992, abandoned, said application No. 07/892,393, is a continuation of application No. 07/605,583, Oct. 29, 1990, abandoned, said application No. 07/934,585, is a continuation of application No. 07/734,392, Jul. 23, 1991, abandoned, said application No. 07/915,286, is a continuation of application No. 07/734,404, Jul. 23, 1991, abandoned, said application No. 07/944,764, is a continuation of application No. 07/810,774, Dec. 17, 1991, abandoned, said application No. 08/204,794, is a division of application No. 07/823,797, Jan. 22, 1992, abandoned, said application No. 08/665,595, is a continuation of application No. 08/161,215, Dec. 2, 1993, abandoned, which is a continuation of application No. 07/874,872, Apr. 28, 1992, abandoned, said application No. 08/166,660, is a continuation of application No. 07/915,134, Jul. 23, 1992, abandoned, said application No. 08/268,869, is a continuation of application No. 08/165,757, Dec. 13, 1993, abandoned, which is a continuation of application No. 07/915,201, Jul. 23, 1992, abandoned, said application No. 07/238,191, is a continuation of application No. 07/915,202, Jul. 23, 1992, said application No. 08/315,315, is a continuation of application No. 07/915,284, Jul. 23, 1992, abandoned, said application No. 08/288,656, is a continuation of application No. 07/915,285, Jul. 23, 1992, abandoned.

[51] Int. Cl.[7] .................................................... A61F 13/15
[52] U.S. Cl. ....................................... 604/387; 604/385.1
[58] Field of Search ...................................... 604/373, 384, 604/385.1, 387

[56] References Cited

U.S. PATENT DOCUMENTS

Re. 24,137  4/1956  Jacks .

(List continued on next page.)

FOREIGN PATENT DOCUMENTS 162451  11/1985  European Pat. Off. ............ 604/385.1

(List continued on next page.)

Primary Examiner—Robert A. Clarke
Attorney, Agent, or Firm—Jeffrey V. Bamber

[57] ABSTRACT

A generally thin, flexible sanitary napkin capable of handling medium to high menstrual flows which has a central absorbent hump is disclosed. The hump comprises a longitudinally-oriented elongated medial absorbent hump that projects from the body surface of the sanitary napkin. The sanitary napkin preferably has surrounding absorbent regions outboard of the hump with a caliper of less than or equal to about 5 millimeters. The sanitary napkin preferably has a caliper at the point of maximum amplitude of the hump that is greater than twice the caliper of the surrounding regions. The hump preferably has a caliper of at least about 0.15 inch (about 3.5–4 millimeters). The longitudinal central region of the sanitary napkin preferably has a flexure-resistance that is greater than that of the surrounding regions.

10 Claims, 9 Drawing Sheets

U.S. PATENT DOCUMENTS

| | | |
|---|---|---|
| D. 342,785 | 12/1993 | Farrell . |
| 810,121 | 1/1906 | Green . |
| 810,123 | 1/1906 | Green . |
| 810,128 | 1/1906 | Green . |
| 2,043,325 | 6/1936 | Jackson, Jr. . |
| 2,331,355 | 10/1943 | Strongson . |
| 2,747,575 | 5/1956 | Mercer . |
| 3,115,877 | 12/1963 | Harwood . |
| 3,406,689 | 10/1968 | Hicks et al. . |
| 3,528,422 | 9/1970 | Hodas . |
| 3,865,112 | 2/1975 | Roeder . |
| 3,881,490 | 5/1975 | Whitehead et al. . |
| 4,029,100 | 6/1977 | Karami . |
| 4,046,147 | 9/1977 | Berg . |
| 4,079,739 | 3/1978 | Whitehead . |
| 4,166,464 | 9/1979 | Korpman . |
| 4,195,634 | 4/1980 | Disalvo et al. . |
| 4,217,901 | 8/1980 | Bradstreet et al. . |
| 4,425,130 | 1/1984 | DesMarais . |
| 4,445,900 | 5/1984 | Roeder . |
| 4,490,147 | 12/1984 | Malfitano . |
| 4,540,414 | 9/1985 | Wishman . |
| 4,578,069 | 3/1986 | Whitehead et al. . |
| 4,595,392 | 6/1986 | Johnson et al. . |
| 4,605,405 | 8/1986 | Lassen . |
| 4,609,373 | 9/1986 | Johnson . |
| 4,639,254 | 1/1987 | LeGault et al. . |
| 4,654,040 | 3/1987 | Luceri . |
| 4,666,440 | 5/1987 | MalFitano . |
| 4,701,177 | 10/1987 | Ellis et al. . |
| 4,731,066 | 3/1988 | Korpman . |
| 4,758,240 | 7/1988 | Glassman . |
| 4,787,896 | 11/1988 | Houghton et al. . |
| 4,795,453 | 1/1989 | Wolfe . |
| 4,804,380 | 2/1989 | Lassen et al. . |
| 4,828,555 | 5/1989 | Hermansson . |
| 4,848,572 | 7/1989 | Herrera . |
| 4,855,179 | 8/1989 | Bourland et al. . |
| 4,888,093 | 12/1989 | Dean et al. . |
| 4,938,756 | 7/1990 | Salek . |
| 4,950,264 | 8/1990 | Osborn . |
| 5,007,906 | 4/1991 | Osborn et al. . |
| 5,009,653 | 4/1991 | Osborn . |
| 5,057,096 | 10/1991 | Faglione . |
| 5,092,860 | 3/1992 | Pigneul . |
| 5,129,893 | 7/1992 | Thoren . |
| 5,169,394 | 12/1992 | Jean . |
| 5,171,302 | 12/1992 | Buell . |
| 5,188,624 | 2/1993 | Young, Sr. et al. . |
| 5,197,959 | 3/1993 | Buell . |
| 5,234,422 | 8/1993 | Sneller et al. . |
| 5,248,309 | 9/1993 | Serbiak et al. . |
| 5,281,208 | 1/1994 | Thompson et al. . |
| 5,290,262 | 3/1994 | Vukos et al. . |
| 5,300,055 | 4/1994 | Buell . |
| 5,324,278 | 6/1994 | Visscher et al. . |
| 5,334,176 | 8/1994 | Buenger et al. . |
| 5,336,208 | 8/1994 | Rosenbluth et al. . |
| 5,342,337 | 8/1994 | Runeman . |
| 5,376,198 | 12/1994 | Fahrenkrug et al. . |
| 5,411,498 | 5/1995 | Fahrenkrug et al. . |
| 5,466,232 | 11/1995 | Cadieux et al. . |
| 5,484,430 | 1/1996 | Osborn ................................. 604/387 |
| 5,611,790 | 3/1997 | Osborn et al. . |

FOREIGN PATENT DOCUMENTS

| | | |
|---|---|---|
| 0316771 | 5/1988 | European Pat. Off. . |
| 0335253 | 10/1989 | European Pat. Off. . |
| 0405403A2 | 1/1991 | European Pat. Off. . |
| 0425026 | 5/1991 | European Pat. Off. . |
| 0471114A2 | 2/1992 | European Pat. Off. . |
| 0511905 | 11/1992 | European Pat. Off. . |
| 0526225 | 2/1993 | European Pat. Off. . |
| 0162541 | 11/1995 | European Pat. Off. . |
| 2653328 | 4/1991 | France . |
| 0410702 | 5/1934 | United Kingdom . |
| 2191098A | 12/1987 | United Kingdom . |
| WO 91/03999 | 4/1991 | WIPO . |
| WO 91/11164 | 8/1991 | WIPO . |
| WO 92/07535 | 5/1992 | WIPO . |
| WO 92/10984 | 7/1992 | WIPO . |

GENERALLY THIN, FLEXIBLE, SANITARY NAPKIN WITH CENTRAL ABSORBENT HUMP

CROSS-REFERENCE TO RELATED APPLICATIONS

This is a division of application Ser. No. 08/563,879, filed on Nov. 21, 1995, which was a continuation of application Ser. No. 08/007,207, filed on Jan. 22, 1993, which was a continuation-in-part of the following patent applications: U.S. patent application Ser. No. 07/892,393 filed May 28, 1992, (now U.S. Pat. No. 5,324,278 issued Jun. 28, 1994) which was a continuation of U.S. patent application Ser. No. 07/605,583 filed Oct. 29, 1990, abandoned; U.S. patent application Ser. No. 07/934,585 filed Aug. 24, 1992 (now U.S. Pat. No. 5,281,208 issued Jan. 25, 1994), which was a continuation of U.S. patent application Ser. No. 07/734,392 filed Jul. 23, 1991, abandoned; U.S. patent application Ser. No. 07/915,286 filed Jul. 23, 1992 (now U.S. Pat. No. 5,382,245 issued Jan. 17, 1995), which was a continuation of U.S. patent Ser. No. 07/734,404 filed Jul. 23, 1991, abandoned; U.S. patent application Ser. No. 07/734,405 filed Jul. 23, 1991 (now U.S. Pat. No. 5,334,176 issued Aug. 2, 1994); U.S. patent application Ser. No. 07/944,764 filed Sep. 14, 1992, abandoned, which is a continuation of U.S. patent application Ser. No. 07/810,774 filed Dec. 17, 1991, abandoned; U.S. patent application Ser. No. 08/204,794 filed Mar. 2, 1994, pending, which is a divisional of U.S. patent application Ser. No. 07/823,797 filed Jan. 22, 1992, abandoned; U.S. patent application Ser. No. 08/665,595 filed Jun. 18, 1996, which is a continuation of U.S. patent application Ser. No. 08/161,215 filed Dec. 2, 1993, abandoned, which was a continuation of U.S. patent application Ser. No. 07/874,872 filed Apr. 28, 1992, abandoned; U.S. patent application Ser. No. 07/882,738 filed May 14, 1992, pending. U.S. patent application Ser. No. 07/915,133, filed Jul. 23, 1992 now U.S. Pat. No. 5,824,004; U.S. patent application Ser. No. 08/166,660 filed Dec. 13, 1993, pending, which is a continuation of U.S. patent application Ser. No. 07/915,134 filed Jul. 23, 1992, abandoned; U.S. patent application Ser. No. 08/268,869 filed Jun. 30, 1994, pending, which is a continuation of U.S. patent application Ser. No. 08/165,757 filed Dec. 13, 1993, abandoned, which was a continuation of U.S. patent application Ser. No. 07/915,201 filed Jul. 23, 1992, abandoned; U.S. patent application Ser. No. 08/238,191 filed May 4, 1994, pending, which is a continuation of U.S. patent application Ser. No. 07/915,202 filed Jul. 23, 1992, abandoned; U.S. patent application Ser. No. 08/315,315 filed Sep. 29, 1994, pending, which is a continuation of U.S. patent application Ser. No. 07/915,284 filed Jul. 23, 1992; U.S. patent application Ser. No. 08/288, 656 filed Aug. 10, 1994, pending, which is a continuation of U.S. patent application Ser. No. 07/915,285, Jul. 23, 1992 abandoned; U.S. patent application Ser. No. 07/957,575 filed Oct. 7, 1992, pending; and U.S. patent application Ser. No. 07/966,240 filed Oct. 26, 1992, abandoned.

FIELD OF THE INVENTION

The present invention relates to absorbent articles, such as sanitary napkins. More particularly, the present invention relates to a generally thin, flexible, sanitary napkin that is provided with a central absorbent hump.

BACKGROUND OF THE INVENTION

This invention is concerned with absorbent articles such as sanitary napkins, pantiliners, and incontinent pads that are designed to absorb and retain liquid and other discharges from the human body and to prevent body and clothing soiling. The present invention is particularly concerned with sanitary napkins having portions that are generally relatively thin and flexible.

Sanitary napkins of a wide variety of shapes and dimensions are currently used by women for the collection of menses and other bodily discharges.

In the past, a number of efforts have been directed at providing sanitary napkins that maintain contact with the wearer's body. One attempt to provide such body contact is disclosed in U.S. Pat. No. 2,747,575 issued May 29, 1956 to Mercer. The Mercer patent discloses a catamenial bandage having a longitudinal hump which bulges towards and may contact the body of the wearer. The catamenial bandage described in the Mercer patent suffers from several disadvantages, however. For instance, the size and shape of the absorbent pad and hump in the Mercer bandage appear to limit the conditions under which the bandage is able to maintain contact with (and conform to) the body of the wearer. The portions of the bandage that lie laterally to the sides of the hump are not thin and flexible. In addition, the hump of the Mercer bandage is made of a cellulosic material, and, as a result, may tend to collapse and become permanently distorted during use.

The current tendency has been to develop sanitary napkins that are increasingly thinner, and thus more comfortable and less obtrusive than prior sanitary napkins. Recently, efforts have been directed at developing thin sanitary napkins which have the capacity to absorb and contain medium to high menstrual discharges. Previously, such discharges could only be handled by relatively thick sanitary napkins. Examples of thin sanitary napkins having capacities great enough to handle medium to high menstrual flows are disclosed in U.S. Pat. Nos. 4,950,264 and 5,009,653, issued to Osborn, III., on Aug. 21, 1990 and Apr. 23, 1991, respectively.

It is also desirable that sanitary napkins, not only maintain contact with, but conform as closely as possible to the wearer's body. Such a body-conforming capability increases the effectiveness of the sanitary napkin by reducing the possibility that menses will travel around the perimeter of the sanitary napkin and leak. There have been a number of recent efforts to provide sanitary napkins and other absorbent articles with improved body-conforming characteristics. In addition to serving as examples of thin sanitary napkins, the sanitary napkins disclosed in the above-mentioned Osborn patents also serve as examples of anatomically-conforming sanitary napkins. While the sanitary napkins disclosed in the Osborn patents work quite well, the search for improved sanitary napkins has continued.

For instance, it is desirable to provide greater absorbent capacity in the target region of a generally thin, flexible, sanitary napkin. It is also desirable to provide better contact between the sanitary napkin and the wearer's body, particularly with the inwardly-facing surfaces of the wearer's labia majora. It is desirable to accomplish these goals while still providing the same level of comfort as a uniformly thin, flexible, pad.

It has been found that the way the sanitary napkin is held in place in the wearer's undergarment has an effect on the ability of the sanitary napkin to maintain contact with the wearer's body. Sanitary napkins are generally fastened to the wearer's undergarments by a pressure sensitive adhesive or other means. The means is stressed when the wearer moves about, because the wearer's undergarments may not move in concert with the body of the wearer, and the sanitary napkin may not flex and twist with the wearer's undergarments. If stressed excessively, the pressure sensitive adhesive, or other means may become detached from the undergarment. If that happens, the sanitary napkin may shift from the desired position and registration with the wearer's vaginal opening. It is, therefore, also desirable to provide the sanitary napkin with a mechanism to accommodate the independence of movement between the body of the wearer and the wearer's undergarment.

It is an object of the present invention to provide a sanitary napkin which is generally thin and flexible and which is absorbent enough to absorb and contain medium to high menstrual flows.

It is another object of this invention to provide a sanitary napkin which readily intercepts menses when discharged by maintaining contact with and conforming to the shape of the female wearer's body, particularly with the inwardly-facing surfaces of the labia majora.

It is an additional object of the present invention to provide a generally thin, flexible, sanitary napkin with extra absorbency in the target region which still offers the enhanced fit and comfort and the low degree of wearing awareness of uniformly thin sanitary napkins.

Finally, it is an object of this invention to provide a sanitary napkin with mechanisms to accommodate the independence of movement between the wearer's body and the wearer's undergarments.

These and other objects of the present invention will be more readily apparent when considered in reference to the following description and when taken in conjunction with the accompanying drawings.

SUMMARY OF THE INVENTION

The present invention is an absorbent article, such as a sanitary napkin. The sanitary napkin of the present invention is a generally thin, flexible, sanitary napkin that is provided with a central absorbent hump.

The sanitary napkin has a principal longitudinal centerline, a principal transverse centerline, a body surface, and a garment surface. A longitudinal central region is disposed along the length of at least a portion of the principal longitudinal centerline. The sanitary napkin has surrounding regions such as longitudinal side regions disposed at least laterally outboard of the longitudinal central region. The sanitary napkin comprises a liquid pervious topsheet, a liquid impervious backsheet joined to the topsheet, and an absorbent core positioned between the topsheet and backsheet. The body surface of the sanitary napkin is provided with a longitudinal medial absorbent hump in the longitudinal central region.

The surrounding regions of the sanitary napkin (or at least portions thereof) preferably have a caliper of less than or equal to about 5 millimeters. The caliper of the sanitary napkin at the point of maximum amplitude of the longitudinal central region is greater than that of the surrounding regions. The sanitary napkin preferably has a caliper at the point of maximum amplitude of the hump which is greater than about two times the caliper of the surrounding regions. The caliper of the sanitary napkin at the point of maximum amplitude is preferably greater than about 0.15 inch (about 3–4 millimeters), and is more preferably between about 4 millimeters and about 15 millimeters (the caliper of the sanitary napkin at this point must, however, always be at least about 2 times greater than that measured at the surrounding regions). The longitudinal central region of the sanitary napkin also has a flexure-resistance that is greater than that of the surrounding regions. The flexure resistance is measured according to the Circular Bend Procedure described in greater detail herein. The longitudinal central region may have a flexure-resistance of up to about 1,000 grams. The surrounding regions preferably have flexure resistances of less than or equal to about 700 grams.

The hump preferably comprises a hump-forming element that provides additional absorbent capacity and liquid acquisition capability in the target region of the pad. The hump also provides the sanitary napkin with a centering/positioning mechanism. The hump preferably maintains the sanitary napkin in close physical contact with the wearer's body, particularly with the inwardly-facing surfaces of the wearer's labia majora. (The inwardly-facing surfaces of the labia majora are those surfaces of the labia majora adjacent the space between the labia majora). The hump-forming element is preferably a compressible and resilient material. The hump-forming element may comprise a material that is different from the material used in the absorbent core. The compressibility allows the hump (or at least the top half of the hump) to narrow and fit comfortably in the space between the wearer's labia. The resiliency allows the hump to better conform to the wearer's body and maintain such contact during wear. The hump-forming element is preferably both wet and dry resilient. This provides the hump-forming element with resistance to collapsing under the conditions encountered during wear.

It was previously believed that the wearer of a generally thin, flexible, sanitary napkin would experience a noticeably unpleasant feeling if such a sanitary napkin was not relatively uniform in thickness and flexibility. Unexpectedly, however, it has been found that the sanitary napkin of the present invention also provides a similar high level of wearing comfort as a uniformly thin, flexible, sanitary napkin.

In addition, in one embodiment, the absorbent article may comprise a sanitary napkin having an absorbent core that separates from the backsheet of the sanitary napkin. The separation of the absorbent core from the backsheet accomodates the independence of movement between the body of the wearer and the wearer's undergarments. In an alternative embodiment, the sanitary napkin is provided with a panty fastener having a configuration that allows the portion of the sanitary napkin containing the hump to separate from the wearer's undergarments to accomodate the independence of movement between the body of the wearer and the wearer's undergargments. In another embodiment, the sanitary napkin may have a transversely segmented hump adapted to better conform to the body of the wearer. In still another embodiment, the sanitary napkin may be extensible in the longitudinal direction, the lateral direction, or both.

DETAILED DESCRIPTION OF PREFERRED EMBODIMENTS

1. Introduction

The present invention relates to absorbent articles, such as sanitary napkins. The sanitary napkin has a longitudinally-oriented elongated absorbent hump on its body surface to provide improved contact with the wearer's body, particularly with the inwardly-facing surfaces of the wearer's labia majora. The hump may be formed at least partially by a hump-forming element that provides extra absorbency in the "target" region where menses are typically deposited. The regions of the sanitary napkin surrounding the hump (the "surrounding regions") are generally thin and flexible.

The term "absorbent article", as used herein, refers to articles such as sanitary napkins, pantiliners, and incontinent pads which absorb and contain body exudates. The term "disposable", as used herein, refers to articles which are intended to be discarded after a single use and preferably recycled, composted, or otherwise disposed of in an environmentally compatible manner. (That is, they are not intended to be laundered or otherwise restored or reused in their entirety as an absorbent article.)

The term "sanitary napkin", as used herein, refers to an article which is worn by females adjacent to the pudendal region and which is intended to absorb and contain the various exudates which are discharged from the body (e.g., blood, menses and urine). Interlabial devices which reside partially within and partially external of the wearer's vestibule are also within the scope of this invention.

The term "inwardly-facing surfaces" of the wearer's labia majora refrs to those surfaces of the labia majora adjacent the space between the labia majora.

Figure 1:
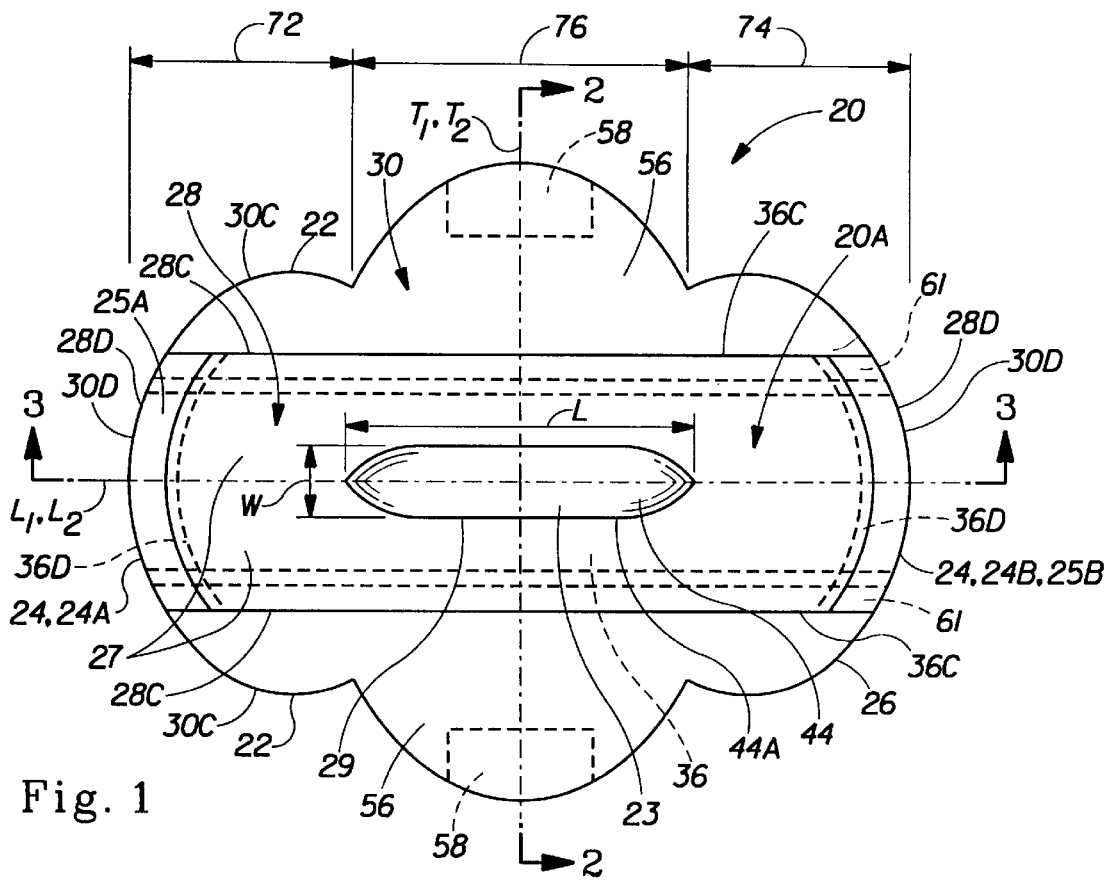
FIG. 1 is a top plan view of a preferred sanitary napkin embodiment of the present invention.
Figure 2:
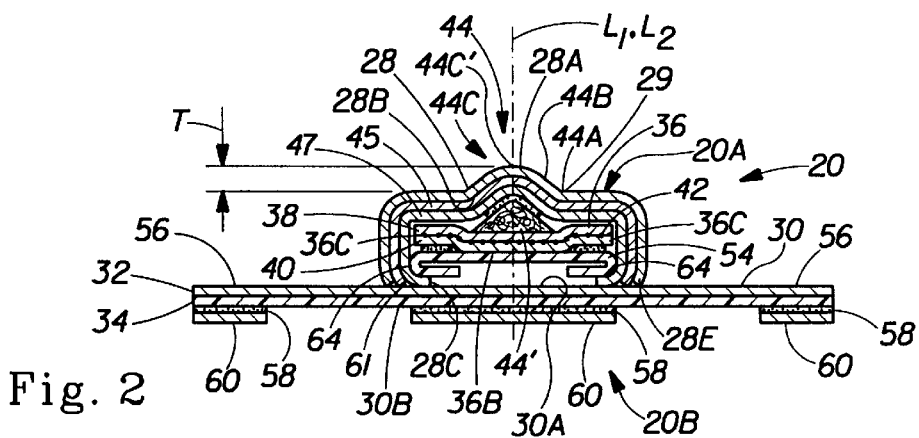
FIG. 2 is a sectional view of the preferred sanitary napkin embodiment shown in FIG. 1 taken along line 2—2 of FIG. 1.
Figure 3:
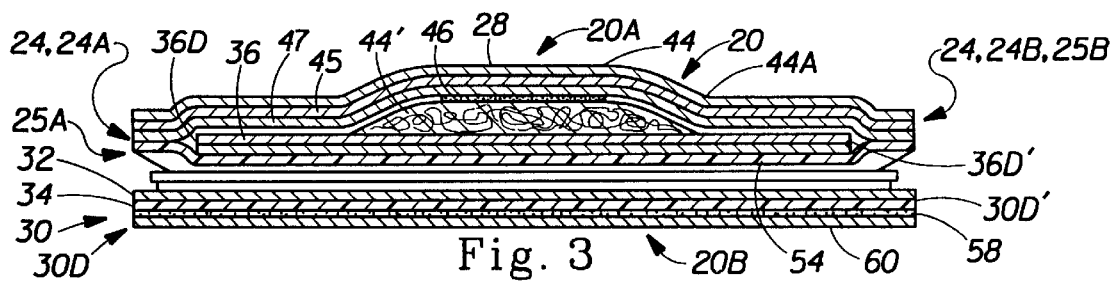
FIG. 3 is a sectional view taken along line 3—3 of FIG. 1.

A preferred embodiment of a sanitary napkin 20 of the present invention is shown in FIGS. 1–3.

The sanitary napkin 20 basically comprises a liquid pervious topsheet 28, a liquid impervious backsheet 30, and an absorbent core 36 positioned between the topsheet 28 and the backsheet 30. A longitudinally-oriented elongated, preferably resilient, medial (or central) absorbent hump 44 protrudes from the body surface 20A of the sanitary napkin 20. A garment surface 20B is on the opposite side of the sanitary napkin and is intended to be placed adjacent to the wearer's undergarments when the sanitary napkin 20 is worn.

The sanitary napkin 20 has two centerlines, a principal longitudinal centerline $L_1$ and a principal transverse centerline $T_1$. The terms "longitudinal" and "transverse" are defined in U.S. Pat. No. 5,007,906 entitled "Decoupled Sanitary Napkin, issued to Osborn, et al. on Apr. 16, 1991. (The term "lateral" is used herein interchangeably with the term "transverse".) The sanitary napkin 20 has a longitudinal dimension that runs in the general direction of the principal longitudinal centerline $L_1$, and a (typically shorter) transverse dimension that runs in the general direction of the principal transverse centerline $T_1$. The sanitary napkin 20 has two spaced apart longitudinal edges 22 and two spaced apart transverse or end edges (or "ends") 24 which form its periphery 26. When the sanitary napkin 20 is worn, one of the end edges 24A, will be oriented toward the front of the wearer, the other end edge 24B, will be oriented toward the rear of the wearer.

The sanitary napkin 20 has a longitudinal central region 23 disposed along the length of at least a portion of the principal longitudinal centerline $L_1$ (and preferably centered about the same). The longitudinal central region 23 is the region of the sanitary napkin 20 that contains the absorbent hump 44. Thus, the boundaries of the longitudinal central region 23 will ordinarily coincide with the perimeter 29 defined by the base 44A of the hump 44. (The perimeter 29 of the hump 44 is located where the elevation of the topsheet 28 changes due to the presence of the hump 44). The size and shape of longitudinal central region 23, therefore, depend on the plan view dimensions of the hump 44.

The surrounding regions 27 are the significant absorbent portions of the sanitary napkin that lie outboard of the longitudinal central region 23. The term "outboard" means positioned away from the intersection of the principal longitudinal and transverse centerlines, $L_1$ and $T_1$. The surrounding regions 27 may be referred to an "longitudinal side regions" (or "side regions") 27 because they will typically lie at least transversely outboard of the hump 44 so that they are on both longitudinal sides of the hump 44 and the sanitary napkin (hence the name "longitudinal side regions"). The surrounding regions 27 can, however, lie outboard of the longitudinal central region 23 in either a longitudinal direction (i.e., outside the ends of the hump in the end regions 72 and 74), a transverse direction (i.e., outside the longitudinal edges of the hump 44, for instance, if the hump 44 ran the entire length of the absorbent core 36), or both (the latter being shown in FIG. 1). The surrounding regions 27, thus, need not completely surround the all sides of the hump 44.

The sanitary napkin 20 is said to be "generally" thin and flexible. When the sanitary napkin 20 is described in this manner, it is meant that the surrounding regions 27 of the sanitary napkin are relatively thin and flexible though the longitudinal central region 23 may be relatively thick and inflexible in comparison. The embodiment of the sanitary napkin 20 shown in the drawings is intended to be an example of a generally thin sanitary napkin 20. It should be understood when viewing the drawings, however, that the number of layers of material shown cause the sanitary napkin 20 to appear much thicker than it actually is.

The sanitary napkin 20 of the present invention can be constructed generally in accordance with U.S. Pat. Nos. 4,950,264 and 5,009,653 both entitled "Thin, Flexible Sanitary Napkin", issued to Osborn on Aug. 21, 1990 and Apr. 23, 1991, respectively. The phrase "constructed generally in accordance with" means that the sanitary napkin may have at least some of the same components and properties of the sanitary napkins described in these references. If the sanitary napkin of the present invention is constructed generally in accordance with the descriptions in any of the foregoing references, however, it must be provided with the longitudinally-oriented absorbent hump and the other unique features described herein.

(It should be understood that the various components of the sanitary napkins described in the above references may be described with slightly different terminology than is used herein. The drawings and elements contained herein, however, can be compared to those of the references to readily locate the corresponding components described in this patent application. It is expressly not admitted, however, that any of the documents incorporated by reference herein teach or disclose the present invention.)

2. The Individual components of the Sanitary Napkin

The individual components of the sanitary napkin 20 will now be looked at in greater detail.

A. The Topsheet

The topsheet 28 is the component of the sanitary napkin which is oriented towards and contacts the wearer's body, and receives bodily discharges. The topsheet 28 overlies, and is folded around several of the other components of the sanitary napkin. When the sanitary napkin 20 is in use, the topsheet is in close proximity to the body of the user.

The topsheet 28 has a body-facing side (or "body surface") 28A and a core-facing side 28B. The body-facing 28A of the topsheet 28 generally forms at least a portion of the body-contacting surface ("body surface") 20A of the sanitary napkin 20. The topsheet 28 has two longitudinal edges 28C and two end edges 28D. (A similar numbering system will be used for the other components of the sanitary napkin. That is, the side of the component facing the wearer's body will be designated by the number of the component and a reference letter "A", the side facing the wearer's undergarments by the number of the component and the letter "B", and the side and end edges by the number of the component and the reference letters "C" and "D" respectively.)

The topsheet 28 is liquid pervious and should be flexible and nonirritating to the skin. As used herein the term "flexible" refers to materials which are compliant and readily conform to the shape of the body or respond by easily deforming in the presence of external forces. Preferably the topsheet 28 is not noisy, to provide discretion for the wearer. The topsheet 28 should be sanitary, clean in appearance and somewhat opaque to hide the bodily discharges collected in and absorbed by the core 36. The topsheet 28 should further exhibit good strikethrough and rewet characteristics, permitting bodily discharges to rapidly penetrate through to the core 36, but not flow back through the topsheet 28 to the skin of the wearer.

A suitable topsheet 28 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet comprises an apertured formed film. Apertured formed films are preferred for the topsheet because they are pervious to body exudates and yet nonabsorbent and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. The preferred topsheet for the present invention is the formed film described in one or more of the above patents and marketed on sanitary napkins by the Proctor & Gamble Company of Cincinnati, Ohio as "DRI-WEAVE".

In a preferred embodiment of the present invention, the body surface of the formed film topsheet is hydrophilic. This helps liquids transfer through the topsheet faster than if the body surface was not hydrophilic and diminishes the likelihood that menstrual fluid will flow off the topsheet rather than into the absorbent core. In a preferred embodiment, surfactant is incorporated into the polymeric materials of the formed film topsheet such as is described in U.S. patent application Ser. No. 07/794,745, "Absorbent Article Having a Nonwoven and Apertured Film Coversheet" filed on Nov. 19, 1991 by Aziz, et al. Alternatively, the body surface of the topsheet can be made hydrophilic by treating it with a surfactant such as is described in the above reference U.S. Pat. No. 4,950,254 issued to Osborn.

Figure 15:
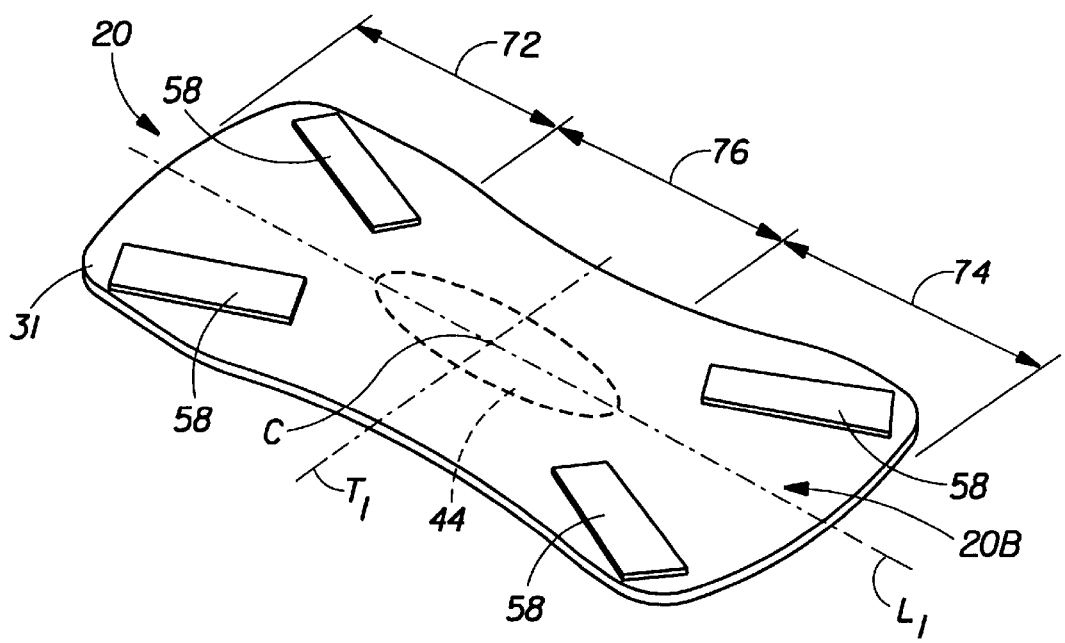
FIG. 15 is a schematic perspective view of a sanitary napkin having a preferred adhesive pattern.

The sanitary napkin 20 may also be extensible (as shown in FIG. 15 and described below in Section 4C). One preferred topsheet 28 for use in extensible embodiments is one which is made in accordance with U.S. Pat. No. 4,463,045 and ring rolled to provide it with a degree of extensibility. Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 filed by Gerald M. Weber et al. on Feb. 28, 1991, U.S. patent application Ser. No. 07/662,537 filed by Kenneth B. Buell et al. on Feb. 28, 1991, and U.S. patent application Ser. No. 07/662,543 filed by Gerald M. Weber et al. on Feb. 28, 1991. The fold lines in the corrugations of the topsheet should run in the transverse direction so the topsheet is longitudinally extensible. Other suitable extensible topsheet materials are described in the "Stretchable Absorbent Article" patent applications incorporated by reference in Section 4E below.

B. The Absorbent Core

The absorbent core 36 is the means for collecting and containing bodily discharges, particularly menses, deposited thereon or which otherwise traverse through the liquid permeable topsheet 28.

The absorbent core 36 may be any absorbent means which is capable of absorbing or retaining liquids (e.g., menses and/or urine). As shown in FIG. 1, the absorbent core 36 has a body-facing side (or "first major surface" 36A), a garment-facing side (or "second major surface") 36B, two longitudinal edges (or "side edges") 36C and two transverse or end edges 36D. The absorbent core 36 may be manufactured in a wide variety of sizes and shapes (e.g., rectangular, oval, hourglass, dog bone, asymmetric, etc.).

In the preferred embodiment shown in FIGS. 1–3, the absorbent core 36 is a laminate comprised of a layer of superabsorbent polymer material in the form of particles 42 disposed between two air-laid tissues, first and second tissue layers (or "upper" and "lower" tissue layers), 38 and 40. The first and second tissue layers 38 and 40 provide containment of the superabsorbent polymer material 42, improve lateral wicking of the absorbed exudates throughout the absorbent core 36 and provide a degree of absorbency.

The absorbent core 36 may, however, be made from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; thermally bonded air-laid fibers; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; European Patent Application No. 0 198 683, The Proctor & Gamble Company, published Oct. 22, 1986 in the name of Duenk, et al.; U.S. patent application Ser. No. 07/810,774 entitled "Absorbent Article Having Fused Layers", filed Dec. 17, 1991 in the names of Cree, et al.; U.S. patent application Ser. No. 07/944,764 filed in the names of Cree, et al. (P&G Case 4546R); U.S. patent application Ser. No. 07/957,575 filed in the names of Cree, et al. on Oct. 7, 1992 (P&G Case 4735); and U.S. patent application Ser. No. 07/966,240 filed in the names of Ahr, et al. on Oct. 26, 1992 (P&G Case 4750).

In embodiments of the sanitary napkin capable of extensibility, one preferred absorbent core 36 is a laminate as described above which is slitted or partially slitted for longitudinal extensibility as shown in FIG. 15 in the accompanying drawing figures. This slitted or partially slitted core is described in greater detail in the Capillary Channel Fiber patent applications described in Section 4C. Other suitable extensible core materials are described in the "Stretchable Absorbent Article" patent applications incorporated by reference in Section 4E below.

C. The Backsheet

The backsheet 30 prevents discharges collected by and contained in the sanitary napkin 20, and particularly discharges absorbed by the core 36, from escaping the sanitary napkin 20 and soiling the clothing and bedding of the wearer.

The backsheet 30 may be any flexible, liquid resistant, preferably liquid impervious material, such as a polyolefinic film, although other flexible liquid impervious materials may also be used. Preferably the backsheet 30 is not noisy, to provide discretion for the wearer. The backsheet 30 may permit vapors to escape from the absorbent core 36 (i.e., it may be breathable) while still preventing exudates from passing through the backsheet 30. The backsheet 30 may alternatively be impervious to malodorous gases generated by absorbed bodily discharges, so that the odors do not escape and become noticed by the wearer and others.

The backsheet 30 may comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385. The backsheet is preferably embossed and/or matte finished to provide a more clothlike appearance.

The backsheet 30 has a core-facing side 30A and a garment side 30B. At least a portion of the core-facing side 30A of the backsheet 30 will ordinarily face the core 36. It is also within the scope of the present invention for portions of the core-facing side 30A of the backsheet 30 (such as wings 56) to be folded so that they may not necessarily always face the core 36. The core-facing side 30A is generally the side of the backsheet 30 that is joined to the topsheet 28 and/or the core 36. The garment side 30B of the backsheet 30 generally forms the garment surface 20B of the sanitary napkin 20.

In the preferred embodiment of the sanitary napkin 20 illustrated in FIGS. 1–3, the backsheet 30 is preferably comprised of two layers. As shown in FIG. 2, the backsheet 30 may comprise a first layer 32 of lofted material disposed on the core-facing side 30A of the backsheet 30. The purpose of the first layer 32 is to provide a comfortable, non-irritating surface against the body of the wearer. The lofted layer may be comprised of any suitable material, such as a nonwoven material. Preferably, the lofted layer comprises a hydrophobic nonwoven material. The second layer 34 may be disposed on the garment side 30B of the backsheet 30, and may comprise a fluid impervious film. A low density polyethylene material such as Tredegar Film Products film model XP-39385 has been found particularly well suited for this second layer. The backsheet 30 may also be made of a soft, cloth-like material which is hydrophobic relative to the topsheet 28. A polyester or polyolefinic fiber backsheet 30 has been found to work well. A particularly preferred soft, cloth-like backsheet 30 material is a laminate of a polyester nonwoven material and a film such as the film described in U.S. Pat. No. 4,476,180 issued to Wnuk on Oct. 9, 1984.

A preferred backsheet 30 for use in an extensible sanitary napkin is an extended adhesive film Formula #198-338 manufactured by the Findley Adhesives Company of Wauwatosa, Wis. This extended adhesive film is described in greater detail in the Capillary Channel Fiber patent applications. Other suitable extensible backsheet materials are described in the "Stretchable Absorbent Article" patent applications incorporated by reference in Section 4E below.

D. The Absorbent Hump

The longitudinally-oriented elongated absorbent hump ("absorbent hump", or "hump") 44 on the body surface 20A of the sanitary napkin 20 is shown in FIGS. 1–3.

The hump 44 is particularly useful in fitting into the space between the wearer's labial tissue. The hump 44 is intended to remain in contact with the surfaces of the wearer's labia majora adjacent the space between the labial tissue to more readily intercept menses and other bodily discharges when they leave the wearer's body. The hump 44 may be of such a size that it also at least partially fits against or in the wearer's perineum. Since the hump 44 will be in close proximity to the wearer's body, it should preferably be relatively soft. The hump 44 should preferably be capable forming a good fit and conforming to the shape of the space defined by the inwardly-facing surfaces of the wearer's labia majora.

The hump 44 may be at least partially comprised of (that is, it may be formed by) portions of one or more of the components of the sanitary napkin 20. The hump 44 can be formed by portions of one or more of any of the following components: the topsheet 28, the absorbent core 36, the backsheet 30, or any additional layers described herein that lie between the topsheet 28 and the backsheet 30. Alternatively, or additionally, the hump 44 can be at least partially formed by a hump-forming element such as that designated 44' in the drawings.

The hump 44 is preferably at least partially absorbent. The hump 44 is considered to be "absorbent", for the purposes of the present invention, if any portion of the hump 44 is absorbent. It is not necessary that all portions of the hump 44 be absorbent. however. For instance, the hump 44 will be considered to be "absorbent" even when the topsheet 28 comprises a formed film that is not inherently absorbent itself, as long as one of the underlying components that forms the hump 44 is absorbent.

The hump 44 is "longitudinally-oriented" and "elongated". The terms "longitudinal" and "longitudinally-oriented", as used herein, mean that the hump 44 is oriented so that its largest dimension is oriented in the longitudinal direction. The term "elongated", as used herein, means that the hump 44 is long in proportion to its width. The hump 44 has its own longitudinal and transverse centerlines $L_2$ and $T_2$ (shown in FIG. 1). (When the hump-forming element 44' defines the shape of the hump 44, the hump-forming element 44' will generally also have longitudinal and transverse centerlines of its own. These are typically the same as those of the hump 44.)

The location or position of the hump 44 is shown in FIG. 1. The hump 44 is centered on top of the body surface 20A of the sanitary napkin 20. In such a case, the longitudinal and transverse centerlines of the hump $L_2$ and $T_2$ coincide with the principal longitudinal and transverse centerlines $L_1$ and $T_1$ of the sanitary napkin 20. The hump 44 may alternatively be positioned in other embodiments so that it is offset from either the principal longitudinal or transverse centerlines of the sanitary napkin 20. Preferably, the hump 44 is at least generally centered about the principal longitudinal centerline $L_1$ of the sanitary napkin 20. (That is, the hump 44 is central or "medial", or midway between the longitudinal edges 22 of the sanitary napkin 20). This enables the hump 44 to be positioned into the space between the wearer's labial tissue. The hump 44, however, does not have to be centered relative to the principal transverse centerline $T_1$ of the sanitary napkin 20. The hump 44 may, for instance, be offset from the principal transverse centerline when the sanitary napkin is asymmetrical about the principal transverse centerline. Preferably, however, at least part of the hump 44 is sufficiently centered relative to the principal transverse centerline that part of the hump 44 is located in the central region 76 of the sanitary napkin 20. The term "central region" refers to a transverse section of the sanitary napkin. (The term "central region" is distinguishable from the term "longitudinal central region" 23 used herein. The term central region is defined in U.S. Pat. No. 4,690,680 issued to Higgins on Sep. 1, 1987.)

The hump 44 can be of any shape provided it at least partially fits into the space between the wearer's labial tissue. The hump 44 can be either symmetrical or asymmetrical about its longitudinal and transverse centerlines $L_2$ and $T_2$. In the preferred embodiment shown in FIGS. 1–3, the hump 44 is symmetrical about both. (When discussing the shape of the hump 44, it should be understood that when a hump-forming element 44' is used, the shape of the absorbent hump 44 will generally be similar to that of the hump-forming element 44'. There are situations when the shapes of the hump 44 and the hump-forming element 44' will differ somewhat, however. As one example, when the hump-forming element 44' is cylindrical, because certain components of the sanitary napkin 20 will be draped over the hump-forming element 44', the hump 44 may only take the shape of the upper portion of the cylindrical shape.) Some suitable shapes are described below.

The plan view shape of the hump 44 (that is, the shape of the absorbent hump 44 when viewed from directly above when the sanitary napkin 20 is in its flat, laid out condition) is shown in FIG. 1. The plan view shape of the hump 44 can be cigar-shaped (shown in FIG. 1), rectangular, oval, or some other suitable shape.

Figure 7:
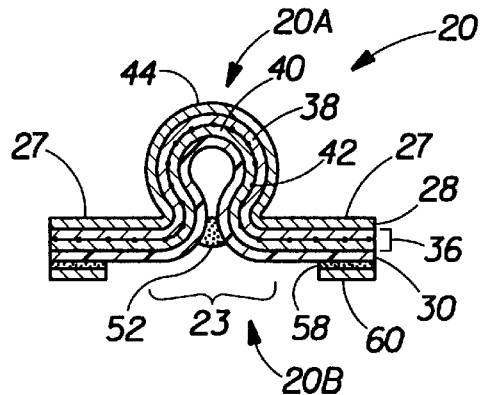
FIG. 7 is a sectional view of an alternate embodiment sanitary napkin taken at an angle similar to that of FIG. 2 in which the hump is created by laterally gathering portions of the central region of the sanitary napkin and securing them by adhesive.
Figure 8:
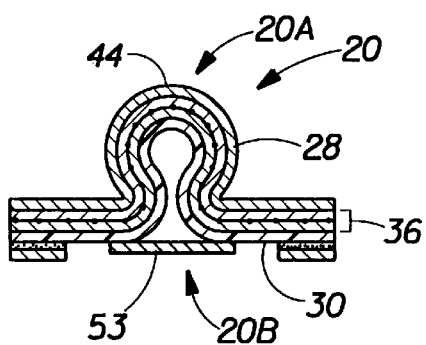
FIG. 8 is a sectional view of an alternate embodiment sanitary napkin taken at an angle similar to that of FIG. 2 in which the hump is created by laterally gathering portions of the central region of the sanitary napkin and securing them by a separate retaining means.
Figure 9:
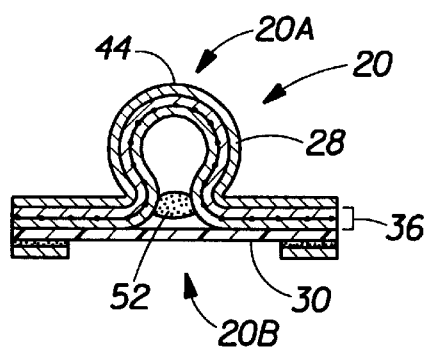
FIG. 9 is a sectional view of an alternate embodiment sanitary napkin taken at an angle similar to that of FIG. 2 in which the hump is created by laterally gathering the topsheet and core only of the sanitary napkin.

The transverse cross-sectional shape of the hump 44 is shown in FIG. 2. The hump 44 has sides which are slightly concave inward which taper to a rounded top surface. The hump 44 could, alternatively, be "box-shaped" so that it has a generally rectangular transverse cross-section. In still other alternatives, the hump 44 could have a cross-section that is semi-circular (for instance, if the hump-forming element 44' is cylindrical). Alternatively, the transverse cross-sectional shape could be parabolic, triangular, in the shape of a modified rectangle that has straight side edges and a rounded top, or any other suitable shape. In still other alternatives, (as shown in FIGS. 7–9) the sides of the hump 44 could be concave outward.

The longitudinal cross-section of the absorbent hump 44 can also take various different shapes. These include, but are not limited to shapes in which the hump 44 is generally rectangular is longitudinal cross-section (for instance, if the hump-forming element 44' is rectangular or cylindrical), and those in which the hump 44 is tapered. FIG. 3 provides an example of a hump 44 which is tapered from its transverse centerline $T_2$ toward both ends of the hump 44.

The hump 44 has a longitudinal dimension (length) L, a transverse dimension (width) W, and a vertical or z-direction dimension ("thickness" or "height") T. (These are shown in FIGS. 1 and 2.) The length L of the hump 44 is measured longitudinally from the most outboard point at the base 44A of the hump on one end of the hump to a similar point on the other end of the hump 44. The width W of the hump 44 is generally measured transversely from the most outboard point on one side of the hump 44 to a similar point on the other side of the hump 44.

The portions of the sanitary napkin at the base 44A of the hump used for the foregoing measurements are located at those places where there is a visible change in direction or degree of curvature or height in the plane defined by the surrounding regions 27. It should also be understood that if the transverse cross-sectional shape of the hump 44 is tapered, the width of the hump 44 may vary between the top of the hump to the base of the hump 44. The hump 44 may, therefore, have different widths (and other dimensions) depending on the portion of the hump 44 that is measured. For instance, the width can be measured using two points which lie in the plane of the base 44A of the hump. Alternatively, the width can be measured in any other plane which cuts through the hump 44 and is parallel to the plane of the base of the hump 44.

The height T of the hump 44 is the perpendicular distance from the top surface of the topsheet 28 at the base 44A of the hump 44 to the point of maximum amplitude 44C' on the top 44C of the hump 44. The caliper of the hump 44 also includes the thickness of portions of the sanitary napkin which lie under the hump. (Thus, the height T of the hump 44 differs from the caliper of the hump 44. The caliper will typically be used to express the entire thickness of the sanitary napkin at the hump because it is easiest to measure.)

The dimensions of the hump 44 can vary between certain limits. The preferred dimensions of the hump 44 are provided below. In some cases, these dimensions may be expressed in terms of the dimensions of the hump-forming element 44'. This may be done because it may be easier to measure the dimensions of such an element. Any of the following dimensions which are expressed in terms of the dimensions of the exterior dimensions of the hump 44 may, thus, also be used as approximations of the dimensions of the hump-forming element 44' and vice versa. If a hump-forming element 44' is used, however, the exterior dimensions of the hump 44 will generally be slightly greater than the dimensions of the hump-forming element 44'. The exterior dimensions of the hump 44 differ from those of the hump-forming element 44' by the thickness of the components of the sanitary napkin that overlay the hump-forming element 44' and by any additional thicknesses created when these components are positioned or "draped" over the hump-forming element 44'.

The length L of the hump 44 can range from between about 0.75 inch (about 2 cm.) to the length of the absorbent core 36. (The length of the absorbent core 36 can, for example, be about 8 inches (about 20 cm.) to about 8.5 inches (about 22 cm.). Preferably, the length L of the hump 44 is between about 1.5 inches (about 4 cm.) and about 6 inches (about 15 cm.), and more preferably, is between about 1.5 inches (about 4 cm.) and about 4 inches (about 10 cm.), and most preferably is between about 1.5 inches (about 4 cm.) and about 3 inches (about 7.5 cm.). With regard to the length of the hump 44, it should be noted that it is believed that the sanitary napkin 20 will perform better when the length of the hump is shorter than some of the lengths specified above at the high ends of the ranges. The preferred lengths are in the range of between about 1 or 1.5 inches (about 2 or 4 cm.) to about 4 inches (about 10 cm.). More preferred lengths are between about 4 cm. to about 10 cm. A particularly preferred length for the hump is between about 3 cm. and about 8 cm with a length of about 2¾ inches (about 7 cm.) being especially preferred. These typically work better because the hump will fit more completely in the space between the wearer's labial tissue and in the perineal groove. The embodiments having humps 44 longer than these lengths, while still operable, are less preferred because they represent further departures from structures which fit entirely within the space between the wearer's labial tissue and perineal groove.

The width W of the hump 44 may be as great as between about ¼ inch (about 0.5 cm.) and about 2 inches (about 5 cm.), and is more preferably between about ⅜ inch (about 1 cm) to about 2 inches (about 5 cm.), and more preferably still is between about ⅜ inch (about 1 cm.) and about 1¾ inches (about 4.5 cm.) at the base, and most preferably is between about ⅜ inch (about 1 cm.) and about 1½ inch (about 4 cm.). The dimensions of the hump 44 will often decrease from the base 44A of the hump to the top 44C of the hump 44. When the hump 44 tapers from the base 44A to the top 44C as shown in FIG. 2, the top 44C of the hump 44 may resemble the top of a ridge and have a very small width at the point of maximum amplitude 44C'. The dimensions of the portions of the hump 44 above the base 44A, particularly (the width of) those portions that comprise the upper half of the hump 44, may more closely approximate the dimensions of the hump-forming element 44 (described below) than the dimensions of the lower half of the hump. (The "upper half" of the hump refers to those portions spaced greater than or equal to ½ T from the base.) That is because these portions of the hump 44 are more likely to be the portions of the hump that at least partially fit into the space between the wearer's labia. In still other alternative embodiments, the size of the base of the hump 44 could also be within the ranges of dimensions given below for the hump-forming element 44'.

The caliper of the portions of the sanitary napkin 20 containing the hump 44 can be measured at different portions of the hump 44. Preferably, the caliper of the hump 44 is measured at the point of maximum amplitude. The caliper of the point of maximum amplitude 44C' of the hump 44 is greater than that of the surrounding regions 27. The caliper of the sanitary napkin 20 at the point of maximum amplitude 44C' of the hump 44 is preferably greater than about 2 times the caliper of the surrounding regions 27 of the sanitary napkin. (The point of maximum amplitude 44C' is typically located along the longitudinal centerline of the hump 44.) The sanitary napkin 20 preferably has a caliper at the point of maximum amplitude of the hump of at greater than about 3 millimeters, more preferably between about 4 millimeters and about 15 millimeters, still more preferably between about 5 millimeters and about 10 millimeters, and most preferably between about 5 millimeters and about 8 millimeters. The thickness T of the hump 44 can be calculated by subtracting the caliper of the surrounding regions 27 at the base 44A of the hump 44 from the caliper of the hump.

The sanitary napkin (as discussed above) may have a hump 44 that is at least partially formed by a hump-forming element 44'. The hump-forming element 44' not only partially forms the hump 44, it may also provide extra absorbency in the target region of the sanitary napkin 20 (the region where menses and other bodily discharges are typically deposited).

Figure 6:
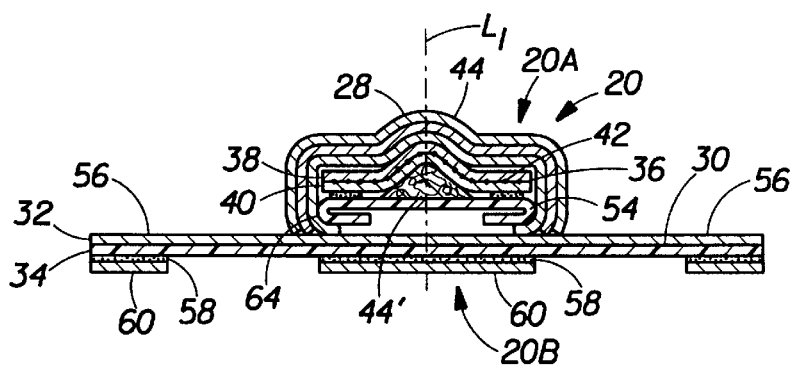
FIG. 6 is a sectional view of a sanitary napkin taken from a similar angle to that of the sanitary napkin of FIG. 2 which shows an alternative placement of the hump-forming element used in the sanitary napkin of the present invention.

The hump-forming element 44' shown in FIGS. 1–3 is positioned on top of (i.e., above) the absorbent core 36 and under an optional wipe acquisition sheet 45 and wet-laid tissue 47 (described in greater detail below). In alternative embodiments, the hump-forming element 44' can be positioned between nearly any of the other components or layers described herein. For instance, the hump-forming element 44' can be positioned between one of the tissue layers (such as either 38 or 40) that comprises the absorbent core 36 and the layer of superabsorbent material particles 42 in the core. In such an embodiment, the hump-forming element 44' may be considered to be positioned within the absorbent core 36. The hump forming element 44' also may be positioned adjacent to one of the faces of the absorbent core 36. The hump-forming element 44' can be integral with the absorbent core 36 (i.e., it can be a part of the absorbent core 36), or it can be a separate element from the absorbent core 36. In still other embodiments (such as shown in FIG. 6), the hump-forming element 44' may be positioned below the absorbent core 36. In still other alternative embodiments, the hump-forming element 44' can comprise a longitudinally-oriented tube that is attached to the body surface of the sanitary napkin. Such an embodiment is shown in FIG. 19 of U.S. patent application Ser. No. 07/874,872, filed in the name of Osborn on Apr. 28, 1992 (of which the present application is a continuation-in-part).

The hump-forming element 44' will normally be a lofted (i.e., relatively thick) component. The hump-forming element 44' should also preferably be soft and non-irritating to the wearer since it may be placed in relatively close contact with the wearer's body. The hump-forming element 44' may also be somewhat flexible. However, it is not necessary for the hump-forming element 44' to be as flexible as the surrounding regions 27 of the sanitary napkin.

The hump-forming element 44' may also be absorbent. The hump-forming element 44', however, need not be absorbent if it is placed under the absorbent core 36. If it is disposed above the core, the absorptive capacity of the hump-forming element 44' should preferably be at least about 0.5 grams at a load of 0 psi.

The hump-forming element 44' preferably should be held in place in the sanitary napkin 20 so that it is prevented from shifting a great deal longitudinally or laterally when the sanitary napkin 20 is worn. The hump-forming element 44' may have some lateral mobility to adjust to non-symmetric anatomy and misplacement of the sanitary napkin in the panty by the wearer. The hump-forming element 44' does not have to be secured to any other component of the sanitary napkin 20, however. The hump-forming element 44' could, for instance, be merely fit snuggly between components of the sanitary napkin or within a component of the sanitary napkin. Typically, however, the hump-forming element 44' is secured to the components that lie both above and below it.

The hump-forming element 44' can be secured to these components with any suitable hump-forming element securement means 46, such as an adhesive. The hump-forming element securement means 46 may coincide in area with the area of all the upper and lower surfaces of the hump-forming element 44' (or it may only coincide with a portion of these surfaces). The hump-forming element securement means 46 should not inhibit flow of menses and other exudates to the hump-forming element 44' or to the core 36. If the hump-forming element securement means 46 is an adhesive, the path of flow to the core 36 can be preserved in several ways. These include spreading the adhesive sufficiently thin so that a substantial number of the apertures in the topsheet material are not covered with adhesive. Many types of adhesives are suitable for use as the hump-forming element securement means 46, including water-based adhesives and hot melt adhesives.

The dimensions of the hump-forming element 44' are as follows. The length of the hump-forming element 44' is preferably within approximately the same ranges as the ranges set forth above for the length of the hump 44. The width of the hump-forming element 44' may be between about 0.2 inch (about 0.5 cm.) and about 2 inches (about 5 cm.), more preferably between about ⅜ inch (about 1 centimeter) and about 1.5 inches (about 4 cm.), and most preferably between about ⅜ inch (about 1 centimeter) and about 1¾ inches (about 4.5 cm.). In one preferred embodiment, the width W is in the range of between about 0.1–1.0 cm., and is preferably about ¼ inch (about 0.5 cm). The thickness of the hump-forming element 44' may be between about ⅛ inch (about 0.3 cm.) up to about ⅜ inch (about 1 cm.) or about ½ inch (about 1.3 cm.). In one preferred embodiment, the hump-forming element 44' has a circular cross-section with a diameter of about ⅜ inch (about 1 cm.) so the width W and thickness T are the same.

Figure 6A:
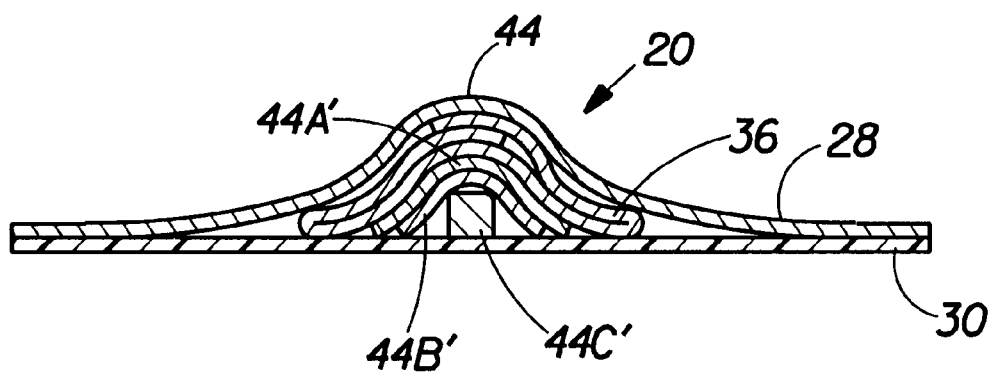
FIG. 6A is a sectional view of a sanitary napkin taken from a similar angle to that of the sanitary napkin of FIG. 2 which shows an alternative embodiment of the hump-forming element.

In another embodiment, the hump-forming element 44' could comprise several separate components which are stacked on top of each other. For instance, as shown in FIG. 6A, the hump-forming element 44' comprises several distinct strips that are positioned under a thin absorbent core 36. The hump-forming element preferably comprises an upper component such as a relatively thin first strip 44A' that is about 1.5 inches (about 4 cm.) wide. The thin strip 44A' is placed on top of a lower component such as a relatively thick, but narrower second strip 44B'. The second strip 44B' is placed on top of a still narrower third strip 44C'. The relatively thick second and third strips serve as a fulcrum around which the core and first strip are bent. The components of the hump-forming element 44' may be made of different materials. In one version of this embodiment, the upper components may be comprised of an absorbent material and the lower components may be non-absorbent, or vice versa. In still other versions, the separate components of this embodiment could be diposed above, within, or partially above and/or within and/or below, the absorbent core. It should be understood that all the various possible arrangements of such separate components are within the scope of the present invention.

The procedure for measuring the dimensions of the hump 44 and the hump-forming element 44' are as follows unless otherwise stated. All measurements are made on newly unpacked absorbent articles. The articles should be removed from their package for at least 30 minutes and handled carefully to avoid compressing, or otherwise affecting the properties of the same. Unless otherwise stated, all tests are performed at 50% humidity and at 73° F. on absorbent articles without any release paper.

The exterior dimensions of the hump 44 other than the caliper are measured using a standard ruler without any load being placed on the sample. The dimensions of the hump-forming element 44' are measured by dissecting the absorbent article and removing the hump-forming element 44' without folding, compressing, or otherwise disturbing the properties of the hump-forming element. The length, width and height of the hump-forming element 44' should then be measured with a standard ruler without load.

The material used for the hump-forming element 44' can be any of those materials specified for use in the absorbent core 36. Preferably, however, the hump-forming element 44' comprises a material that is more resilient than an airfelt mass. One suitable material for use in the hump-forming element 44' is a mass of chemically modified, cross-linked cellulosic fibers such as those described in U.S. Pat. No. 4,888,093 issued Dec. 19, 1989 to Cook, et al. Another suitable material is a tuft of superabsorbent fibers, such as those formerly manufactured by Arco chemical Company of Newton Square, Pa. under the trademark FIBERSORB and those currently manufactured by Courtaulds, Ltd., West Midlands, England, Superabsorbent fibers are discussed more fully in U.S. Pat. No. 4,855,179, issued Aug. 8, 1989, to Bourland, et al. Still other suitable materials for the hump-forming element 44' are the capillary channel fibers (fibers having channels on their exterior surfaces) described in greater detail in EPO Patent Application 391,814, Phillips, et al., published Oct. 10, 1990, and in the Capillary Channel Fiber patent applications described below.

The hump-forming element 44' (or if there is no separate hump-forming element, then the hump 44) should be somewhat compressible. The compressibility is measured according to the following Compression Caliper Test. The Compression Caliper Test is a version of the caliper test set out in U.S. Pat. No. 5,009,653. In the compression caliper test, however, two caliper measurements are taken, an original caliper, and a compressed caliper. The "original caliper" is measured under a 10 gram comparator foot with no test weight. An 80 gram test weight is then placed on the sample with the 10 gram comparator foot, and the caliper is measured. This latter measurement is the "compressed caliper".

$$\text{The Percentage of Original Caliper} = \frac{\text{compressed caliper}}{\text{original caliper}} \times 100\%$$

The hump-forming element 44' is preferably also comprised of a resilient material. The term "resilient", as used herein, means that when the material is compressed under a load of 0.25 psi. for 5 seconds and the compressive forces cause a reduction in the dimension of the material in the direction of the compressive forces, the material returns to at least about 50% of its uncompressed dimension after the load is removed.

Preferably, the hump-forming element (or hump) recovers to greater than or equal to about 85%, and more preferably about 90% of its compressed caliper when measured according to the following Caliper Recovery Test. The Caliper Recovery Test is also a modified version of the caliper test set out in U.S. Pat. No. 5,009,653 issued to Osborn. The "original caliper" is measured under a 10 gram comparator foot with no weight. An 80 gram test weight is then placed on the sample with the 10 gram comparator foot for 5 seconds. The 80 gram test weight is then taken off, and the caliper of the sample is again measured after 30 seconds under the 10 gram comparator foot. The latter caliper measurement is the "recovered caliper".

$$\text{Recovery}(\%) = \frac{\text{recovered caliper}}{\text{original caliper}} \times 100$$

Preferably, the material chosen for the hump-forming element 44' is resilient in the amounts set forth above under wet and dry conditions (i.e., it is wet and dry resilient). If the hump-forming element 44' is wet resilient, it will not collapse when wetted by bodily discharges and will be able to handle initial, as well as subsequent loadings of bodily fluids.

Suitable wet resilient materials include, but are not limited to polyesters, rayons, orlons, and surfactant treated polyolefin fibrous materials. A preferred wet resilient material that can be used for the hump-forming element 44' is a 6 denier polyester fiber batt. Another preferred material is a mixture of FIBERSORB (though not wet resilient by itself) with such a polyester fiber batt. These materials are not only resilient, but they have also been found to be relatively soft and comfortable for the wearer.

Still another preferred material for the hump-forming element 44' is the 6 denier polyester fiber batt described above overlayed (or covered) by a laminate which comprises a layer of superabsorbent polymer material disposed between two air-laid tissues. The laminate used in such an embodiment could comprise part of the absorbent core 36, or it could comprise a laminate which is separate from the absorbent core. In still other alternatives, one or more of the components of the hump-forming element 44' could comprise a foam.

E. Optional Components

The sanitary napkin 20 of the present invention can be provided with any optional additional components that are known in the art or disclosed in the documents incorporated by reference herein.

As shown in FIGS. 1–3, the optional components may include: one or more absorbent layers and/or fluid transporting layers (such as the wipe acquisition sheet or secondary topsheet 45, and the wet-laid tissue 47); an optional interliner 54; or, side flaps or "wings" 56 that are folded around the crotch portion of the wearer's panties when the sanitary napkin 20 is worn (the panties are designated U in the drawings). The sanitary napkin 20 will typically include a fastener (or "fastening means") 58 for attaching the sanitary napkin 20 to the undergarment of the wearer. These optional components are described below.

The wipe acquisition sheet 45 and the wet-laid tissue 47 are described in greater detail in U.S. Pat. No. 5,009,653 issued to Osborn. In alternative embodiments, the wipe acquisition sheet 45 may be comprised of modified or cross-linked cellulosic fibers, or the capillary channel fibers described in greater detail in the Capillary Channel Fiber patent applications.

The optional interliner 54 is described in greater detail in U.S. Pat. No. 5,007.906 entitled "Decoupled Sanitary Napkin" issued to Osborn, et al. on Apr. 16, 1991.

Flaps 56 suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608, 047, entitled "Sanitary Napkin Attachment Means", which issued to Mattingly on Aug. 26, 1986.

The fasteners (or "panty fasteners") 58 may comprise mechanical fasteners, adhesive fasteners, high coefficient of friction materials, or other types of fasteners. One suitable type of fastener is one or more patches of a pressure sensitive adhesive. The adhesive may be applied to the garment side 30B of the backsheet 30 in any suitable pattern. Suitable adhesive configurations are described in greater detail in U.S. Pat. No. 4,917,697; PCT International Patent Application Publication No. WO 92/04000 published in the name of Papa, et al. on Mar. 19, 1992; and in the patent applications filed Jul. 23, 1992 which are incorporated by reference (in Section 4C "Other Alternative Embodiments") below.

A removable cover strip or release liner 60 may be used to cover the adhesive fastener 58 in order to keep the adhesive from sticking to a surface other than the crotch portion of the undergarment prior to use. In alternative embodiments, the panty fastener may be covered by a covering such as a releasable wrapper that also serves as an individual package for the sanitary napkin. Such a wrapper is described in U.S. Pat. No. 4,556,146 issued to Swanson, et al. on Dec. 3, 1985, and in PCT International Patent Application Publication No. 91/18574 published Dec. 12, 1992 in the name of Byrd, et al.

F. Assembly of the Components of the Sanitary Napkin

The topsheet, the backsheet, and the absorbent core may be assembled in a variety of well known configurations (including so called "tube" products and side flap products).

The topsheet 28 and backsheet 30 are generally positioned adjacent the body surface and garment surface, respectively, of the absorbent core 36 (with or without intervening components therebetween). The topsheet and backsheet are preferably joined directly or indirectly to the core, to each other, or to each other and to the core, by attachment means such as those well known in the art. (The term "joined" is defined in U.S. Pat. No. 5,007,906 issued to Osborn, et al.)

FIGS. 1 and 2 show a preferred embodiment of the sanitary napkin 20 in which the topsheet 28, the wet-laid tissue 47, and the wipe acquisition sheet 45 preferably extend beyond the longitudinal side edges 36C of the absorbent core 36 and are wide enough to be folded inward under themselves along their longitudinal edges and joined to the backsheet 30 along their longitudinal edges at a pair of transversely spaced apart longitudinal junctures 61. The remainder of these components are unattached to the backsheet so the unattached portions may move apart from the backsheet. (This feature is described in greater detail in Section 4A "Embodiments Providing for Separation of the Absorbent Core From the Backsheet" below.)

In other embodiments, the topsheet 28 and the backsheet 30 may have length and width dimensions generally larger than those of the absorbent core 36 and be peripherally joined around the core 36. The topsheet 28 and the backsheet 30 may also extend beyond the edges of the absorbent core 36 to form not only portions of the periphery but also side flaps.

The topsheet 28 and/or backsheet 30 may be secured to the absorbent core 36 or to each other by attachment means such as adhesives. Adhesives which have been found to be satisfactory are manufactured by H. B. Fuller Company of St. Paul, Minn. under the designation HL-1258 or H-2031. Such adhesives can be in the form of a uniform continuous layer of adhesive, a patterned layer of adhesive, or an array of separate lines, spirals, or spots of adhesive. The attachment means preferably comprises an open pattern network of filaments of adhesive as is disclosed in U.S. Pat. No. 4,573,986 issued to Minetola, et al. on Mar. 4, 1986. An exemplary attachment means comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989.

Alternatively, the attachment means may comprise heat bonds, pressure bonds, ultrasonic bonds, dynamic mechanical bonds, or any other suitable attachment means or combinations of these attachment means as are known in the art or described in the documents incorporated by reference herein. Suitable alternative attachment means are described in U.S. patent application Ser. No. 07/810,774 entitled "Absorbent Article Having Fused Layers" filed in the name of Cree, et al. on Dec. 17, 1991.

3. Caliper, Flexibility, Capacity, and Other Properties of the Sanitary Napkin

The surrounding regions 27 of the sanitary napkin 20, as noted above, are "generally thin and flexible." The sanitary napkin 20, in spite of its thinness, is capable of handling medium to high menstrual flows.

A. Caliper

The caliper (and flexibility) of the surrounding regions 27 is to be measured by measuring the "significant absorbent portions" of the sanitary napkin.

The term "significant absorbent portions", as used herein, refers to those portions of the sanitary napkin in the main body portion of the napkin (the main body portion comprises the portions of the napkin exclusive of any side flaps) that contain absorbent material therein.

It is these significant absorbent portions that are of interest, rather than any other portions of the sanitary napkin that lie laterally outboard the surrounding regions 27 (an example of these latter portions are where the topsheet and backsheet extend into a seal around the periphery of the sanitary napkin) which do not contain significant absorbent material but which may be more flexible and have calipers less than the calipers of the significant absorbent portions specified herein.

The caliper of a sanitary napkin 20, or various regions thereof, is determined by the following test. At least one measurement is taken in the longitudinal central region of the sanitary napkin at the point of maximum amplitude of the hump, and at least one measurement is taken in the surrounding regions of the sanitary napkin.

A comparator gauge, and specifically the Ames, Model 130 with dial indicator Model 482, available from the B.C. Ames, Company of Waltham, Mass. is needed. The comparator gauge should typically have a circular comparator foot made of aluminum and a weight of 10.0 grams and a contact surface of 5.16 square centimeters. The gauge is provided with an 80.0 gram stainless steel weight to provide a total of 0.25 psi pressure. If due to the plan view shape of the region to be tested, it is not possible to use a circular comparator foot and achieve an accurate measurement of the region, a 1"×¼" rectangular comparator foot should be used and a test weight should be used that provides a total pressure of 0.25 psi. The comparator gauge is zeroed. The weight is placed on the spindle extending above the comparator dial. The comparator foot is raised and the napkin, with any panty adhesive release paper being removed and the adhesive is sprinkled with corn starch, is placed garment surface down on the base plate. The napkin is positioned on the base plate so that when the foot is lowered it is in the region of the napkin for which the measurement is desired. Try to smooth out or avoid any wrinkles in the napkin. Gently lower the foot onto the napkin. Determine the napkin caliper by reading the comparator dial 30 seconds after the foot comes in contact with the napkin.

The surrounding regions 27 have a caliper of less than or equal to about 5 millimeters, preferably less than or equal to about 4 millimeters, and more preferably less than or equal to about 3 millimeters. The caliper of the surrounding regions 27 may also be any of those calipers specified for the "significant absorbent portions" of sanitary napkin described in U.S. Pat. No. 5,009,653 issued to Osborn. (It should be understood that the definition of the term "significant absorbent portions" used herein differs from the term as defined in the Osborn patent in that it includes absorbent portions that may only comprise a single tissue layer or absorbent material.) The caliper of the surrounding regions 27 of the sanitary napkin of the present invention may be increased, in less preferred embodiments, proportional to an increase in the flexure-resistance. If the flexure-resistance is increased to greater than about 400 grams, or even greater than about 500 grams, the caliper may be increased to as much as about 4.0 to about 5.0 millimeters, but preferably is not greater than about 3.0 millimeters.

The caliper of the longitudinal central region 23 of the sanitary napkin, of course, will typically be greater than the calipers specified above because of the presence of the absorbent hump 44. The calipers of the various alternative embodiments of the sanitary napkin as measured along the principal longitudinal centerline are set out in Section 2D above.

B. Flexibility

The sanitary napkin 20 is described as being generally flexible. The term "generally flexible", as used herein, means that the sanitary napkin 20 can have a relatively inflexible longitudinal central region 23, provided it has relatively flexible respective surrounding regions 27 so that the sanitary napkin 20 is comfortable for the wearer.

The flexibility of the various regions of the sanitary napkin is expressed in terms of flexure-resistance. The flexibility is measured according to the Circular Bend Procedure (described in greater detail below). The longitudinal central region 23 preferably has a flexure-resistance of up to: less than or equal to about 1,000 grams, more preferably less than or equal to about 700 grams, even more preferably less than or equal to about 500 grams, and most preferably less than or equal to about 400 grams.

The surrounding regions 27 preferably have flexure resistances of less than or equal to about 700 grams, more preferably less than or equal to about 600 grams, more preferably less than or equal to about 500 grams, more preferably less than or equal to about 400 grams, more preferably less than or equal to about 300 grams, and most preferably less than about 250 grams. The flexure-resistance of the surrounding regions 27 may also be any of those figures specified for the sanitary napkin described in U.S. Pat. No. 5,009,653 issued to Osborn.

The flexure-resistance of the longitudinal central region 23 is often greater than the flexure-resistance of the respective surrounding regions 27. It is possible, however, for a sanitary napkn to have a hump and a longitudinal central region 23 that has the same or lesser flexibility than the surrounding regions. An example of such an embodiment is one in which the hump is provided by a flexible material and one or more stiffer components of the sanitary napkin is removed in the longitudinal central region 27.

The flexure-resistance of the different regions of the sanitary napkin is measured as peak bending stiffness. Peak bending stiffness is determined by a test which is modeled after the ASTM D 4032-82 Circular Bend Procedure. The ASTM procedure is modified for use herein. The Circular Bend Procedure as modified and used for the purposes of the present invention is hereinafter simply referred to as the "Circular Bend Procedure". One version of the Circular Bend Procedure is described in U.S. Pat. No. 5,009,653 issued to Osborn. The Circular Bend Procedure is a simultaneous multi-directional deformation of a material in which one face of a specimen becomes concave and the other face becomes convex. The Circular Bend Procedure gives a force value related to flexure-resistance, simultaneously averaging stiffness in all directions.

In the case of the present invention when carrying out the Circular Bend Procedure, rather than using one set of samples taken from the significant absorbent portions of the sanitary napkin as described in U.S. Pat. No. 5,009,653, separate samples of the sanitary napkins are taken from longitudinal central region 23 and from the surrounding regions 27. The samples are tested and averaged separately so a flexure-resistance value is obtained for the longitudinal central region 23, and a separate value is obtained for the surrounding regions 27.

APPARATUS

The apparatus necessary for the CIRCULAR BEND PROCEDURE is a modified Circular Bend Stiffness Tester, having the following parts:

A smooth-polished steel plate platform which is 102.0× 102.0×6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice.

A force-measurement gauge and more specifically an Instron inverted compression load cell. The load cell has a load range of from about 0.0 to about 2000.0 grams.

An actuator, and more specifically the Instron Model No. 1122 having an inverted compression load cell. The Instron 1122 is made by the Instron Engineering Corporation, Canton, Mass.

NUMBER AND PREPARATION OF SPECIMENS

In order to perform the procedure for this test, as explained below, five representative sanitary napkins are necessary. From one of the five napkins to be tested, some number "Y" of 37.5×37.5 millimeter test specimens are cut. At least one specimen is cut from the portion of the sanitary napkin containing the point of maximum amplitude of the hump thereon, and at least one specimen is cut from the surrounding regions of the sanitary napkin. If due to the plan view shape of the region to be tested, it is not possible to cut a square 37.5×37.5 mm. specimen, any other 1,400 square millimeter size specimen may be used, provided the specimen adequately covers the orifice in the test platform to properly carry out the test.

Specimens having portions in which a topsheet is joined directly to a barrier sheet or which are a laminate of a topsheet, two or less tissue sheets and a barrier sheet, should also not be tested. The reason that these specimens are not tested is due to the realization that prior art napkins exist in which a topsheet is joined to a barrier sheet beyond the edges of an absorbent core in the periphery of the napkin, such portions of which are highly flexible. The present invention is more concerned with the flexibility of the significant absorbent portions of the sanitary napkin. If any of the significant absorbent portions of the sanitary napkin meet the parameters set forth in the appended claims for the particular regions, then the sanitary napkin falls within the scope of the appended claims. A number of different specimens should be tested from each sanitary napkin. In particular, the structurally least flexible portions in the center of the sanitary napkin should be tested as the longitudinal central region. The most flexible portions of the sanitary napkin should be tested when samples of the surrounding regions of the napkin are measured.

The test specimens should not be folded, bent, or compressed by the test person, and the handling of specimens must be kept to a minimum and to the edges to avoid affecting flexural-resistance properties. From the four remaining sanitary napkins, an equal number "Y" of specimens, identical to the specimens cut from the first napkin, are cut. Thus, the test person should have "Y" number of sets of five identical specimens.

PROCEDURE

The procedure for the CIRCULAR BEND PROCEDURE is as follows. The specimens are conditioned by leaving them in a room which is 21±1° C. and 50±2% relative humidity for a period of two hours. The test plate is leveled. The plunger speed is set at 50.0 centimeters per minute per full stroke length. A specimen is centered on the orifice platform below the plunger such that the body surface 20A of the specimen is facing the plunger and the garment surface 20B of the specimen is facing the platform with the release paper removed from any adhesive on the garment surface of the specimen and the adhesive sprinkled with corn starch to eliminate the adhesive tack. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

CALCULATIONS

The peak bending stiffness for each specimen is the maximum force reading for that specimen. Each set of five identical specimens is tested and the five values received for that set are averaged. Thus, the test person now has an average value for each of the "Y" identical sets of specimens tested. If any of the significant absorbent portions of the sanitary napkin have a longitudinal central region and surrounding regions with average for each identical specimen with the requisite flexure-resistances, then the napkin satisfies the parameters of this test.

C. Test Capacity and Total Capacity

The sanitary napkin 20 of the present invention has a liquid capacity great enough to absorb medium to high menstrual flows. The capacity of the sanitary napkin is defined in terms of two capacities, which, depending on the size of the sanitary napkin may be the same: test capacity and total capacity. The definitions of these capacities and the procedures for determining the test and total capacities are the similar to those described in U.S. Pat. No. 5,009,653 issued to Osborn.

The sanitary napkin 20 of the present invention should at least have the test and total capacity described in U.S. Pat. No. 5,009,653. The sanitary napkin should, thus, have a test capacity of at least about 8.0 grams, more preferably at least about 10.0 grams, more preferably still at least about 15.0 grams, and most preferably at least about 18.0 grams. Preferably, the napkin 20 of the present invention has a total capacity of at least about 20.0 grams, more preferably at least about 25.0 grams, and more preferably still at least about 30.0 grams, and most preferably at least about 40.0 grams. Preferably, the sanitary napkin 20 has an even greater test and total capacities when an absorbent hump-forming element 44' is used due to the additional capacity such an element can provide.

The test and total capacities of a sanitary napkin are determined as follows. Any panty adhesive release paper is removed from the napkin to be tested. To determine test capacity, a sample is obtained from a 4.75×14.0 centimeter portion, or any other configuration having 66.5 square centimeters, of the sanitary napkin. The sample is cut from the portion of the sanitary napkin which would be centered under the vaginal orifice when the sanitary napkin is worn. Total capacity is determined using a sample comprising the entire napkin minus any release paper.

The sample is weighed to the nearest 0.1 gram. The sample is then submerged in a beaker of sterile saline (obtainable from the Baxter Travenol Company of Deerfield, Ill.), such that the sample is totally submerged and is not bent or otherwise twisted or folded. The sample is submerged for 10 minutes. The sample is removed from the saline and suspended for two minutes in a vertical position to allow the saline to drain out of the sample. The sample is then placed body-facing surface down onto an absorbent blotter, such as the filter paper #631 available from the Filtration Science Corp., Eaton-Dikeman Division of Mount Holly Springs, Pa. A uniform 17.6 gram per square centimeter load is placed over the sample to squeeze excess fluid out. The absorbent blotter is replaced every 30 seconds until the amount of fluid transferred to the absorbent blotter is less than 0.5 grams in a 30 second period. Next, the sample is weighed to the nearest 0.1 gram and the dry weight of the sample is subtracted. The difference in grams is the test or total capacity of the sample, whichever the case may be.

4. Alternative Embodiments of the Absorbent Article of the Present Invention

A. Embodiments in Which the Hump is Formed by Gathering in Portions of the Sanitary Napkin In alternative embodiments, shown in FIGS. 7–9, the hump 44 is formed by gathering in and securing at least some of the components of the sanitary napkin 20 in the longitudinal central region 23 of the sanitary napkin 20. The gathered in portions of the sanitary napkin 20 can (as shown in FIG. 7) either be secured to each other by a hump-retaining means, such as adhesive 52, to form the hump 44, or they can (as shown in FIG. 8) be secured to a hump-retaining means that comprises a separate component 53 that bridges the secured portions of the napkin.

These embodiments can be constructed generally in accordance with the disclosure of the above-described U.S. Pat. No. 2,747,575 issued to Mercer. However, these embodiments, if constructed generally in accordance with the disclosure of the Mercer patent, differ from the embodiments disclosed in the Mercer patent in several important respects. The embodiments in the form of the present invention have to be formed in generally thin, flexible, sanitary napkins capable of handling medium to high menstrual flows, rather than from a thick pad as disclosed in the Mercer patent. The humps 44 formed have to be in the form of those described herein, and have the same dimensions as those described herein so they will fit comfortably into the space between the wearer's labial tissue. Further, the embodiments of the present invention may be provided with flaps 56 and/or the feature of the present invention in which the absorbent core 36 is capable of separating from the backsheet 30.

In addition, in one version of these embodiments (shown in FIG. 9), one or more (i.e., several, but not all) of the components of the sanitary napkin (such as the topsheet 28 and the absorbent core 36) are gathered in and secured (instead of the entire sanitary napkin being gathered in and secured as in the case of the Mercer patent). It is preferred in such an embodiment that at least some of the components of the sanitary napkin which have been gathered in to form the hump 44 have some absorptive capacity. Thus, such an embodiment would preferably not be constructed by only gathering in and securing a formed film topsheet to form the hump.

B. Embodiments Providing for Separation of the Absorbent Core From the Backsheet In other preferred alternative embodiments, the sanitary napkin can be provided with an absorbent core 36 that is capable of separating from (or "decoupling" from) the backsheet 30 of the sanitary napkin 20 to accomodate the independence of movement between the wearer's body and the wearer's undergarments.

The separation or decoupling of these components refers to a movement of one component apart from another in a direction generally perpendicular to the principal longitudinal and transverse axes of the sanitary napkin (that is, in the "Z-direction").

The concept of the separation (or "decoupling") of components of a sanitary napkin is described in greater detail in U.S. Pat. No. 5,007,906 entitled "Decoupled Sanitary Napkin", issued to Osborn, et al. on Apr. 16, 1991; in PCT International Patent Application Publication No. WO 92/07535 entitled "Sanitary Napkin Having Components Capable of Separation in Use" published in the name of Ronald B. Visscher, et al. on May 14, 1992; and, in U.S. patent application Ser. No. 07/874,872 entitled "Generally Thin, Flexible Sanitary Napkin With Stiffened Center" filed Apr. 28, 1992 in the name of Osborn.

The separation of the core 36 from the backsheet 30 may alternatively be thought of as a separation of the topsheet 28 from the backsheet 30 (as described in U.S. Pat. No. 5,007,906). This is because if the core 36 separates from the backsheet 30, the topsheet 28 (being disposed on the other side of the core 36) will also separate from the backsheet 30.

Figure 4A:
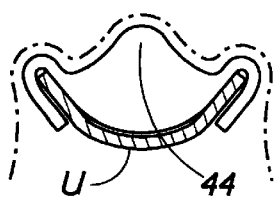
FIG. 4A is a simplified schematic view which shows how the sanitary napkin preferably fits adjacent the wearer's body.
Figure 4:
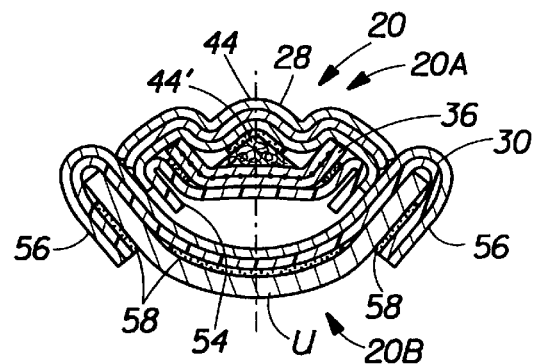
FIG. 4 is a sectional view taken from a similar angle to that of FIG. 2 which shows the separation of the absorbent core of the sanitary napkin from the backsheet.
Figure 5:
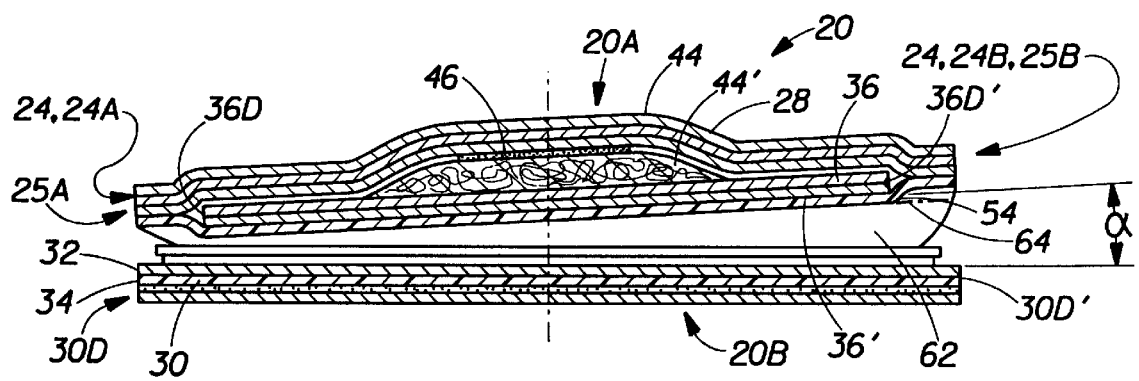
FIG. 5 is a sectional view taken from a similar angle to that of FIG. 3 which shows a side view of the separation of the absorbent core from the backsheet.

The separation or decoupling of the core 36 from the backsheet 30 in the present invention is first shown in FIGS. 4 and 5 of the drawings. The drawings are merely intended to be approximate representations of the configurations that the sanitary napkin 20 may take when it is worn. Thus, the separation of these components may occur in manners in addition to those shown in the drawings. The scope of the present invention includes all of these other configurations and manners of separation. In addition, it should also be understood that the size of various components of the sanitary napkin 20 may be slightly exaggerated in the drawings. This has been done to more clearly show the separation of the components of the sanitary napkin 20.

Figure 10:
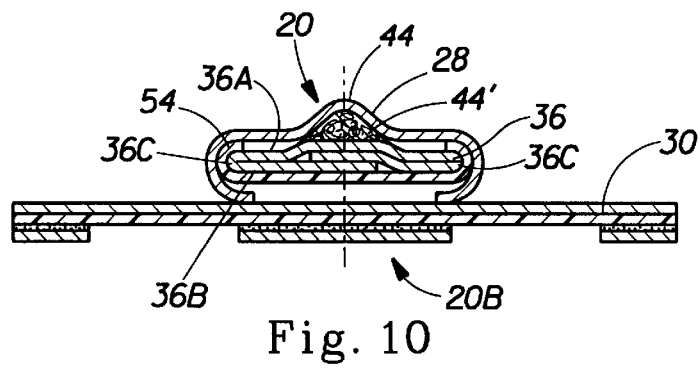
FIG. 10 shows an alternative version of the sanitary napkin of the present invention that has an optional interliner of an alternative configuration.

The sanitary napkin 20 should be provided with an interliner 54 in these embodiments. The interliner 54 is associated with the core 36 and positioned between the core 36 and backsheet 30 in these embodiments. The interliner 54 serves as the first constraint for any bodily discharges that may tend to leave the core 36 and migrate towards the backsheet 30. As shown in FIG. 10, the interliner 54 preferably wraps the longitudinal edges 36C of the core 36. The interliner 54 in this embodiment is preferably joined to body-facing side 36A of the core 36 adjacent the longitudinal edges 36C of the core 36. The characteristics of the interliner 54, the alternative configurations it may take, and the manners of joining it to the core are described in greater detail in the patent publications set forth above that discuss the concept of decoupling.

The separation of the core 36 from the backsheet 30 is possible because of the way the core 36 is joined to the backsheet 30. The core 36 is joined to the backsheet 30 (i.e., directly or indirectly) at longitudinal junctures 61 along the longitudinal edges 36C of the core 36. The core 36 may also be joined to the backsheet 30 along at least one transverse juncture 25. The core 36 is generally otherwise unattached to the backsheet 30 between the longitudinal edges 36C of the core and on at least one end 24 of the sanitary napkin 20. The unattached portion 36' of the core 36 may move apart from the backsheet 30. The transfer juncture 25, if one is present, may be generally coincident with an end edge 24 of the sanitary napkin 20, such as the front end edge 24A. The end edge 24 at which the transverse juncture 25 is located may be referred to as the "joined end edge" 25A. The other end edge is the "unattached end edge" 25B. Typically, the unattached end edge 25B is oriented towards the rear of the wearer when the sanitary napkin 20 is worn (i.e., it is located at end edge 24B).

Figure 12:
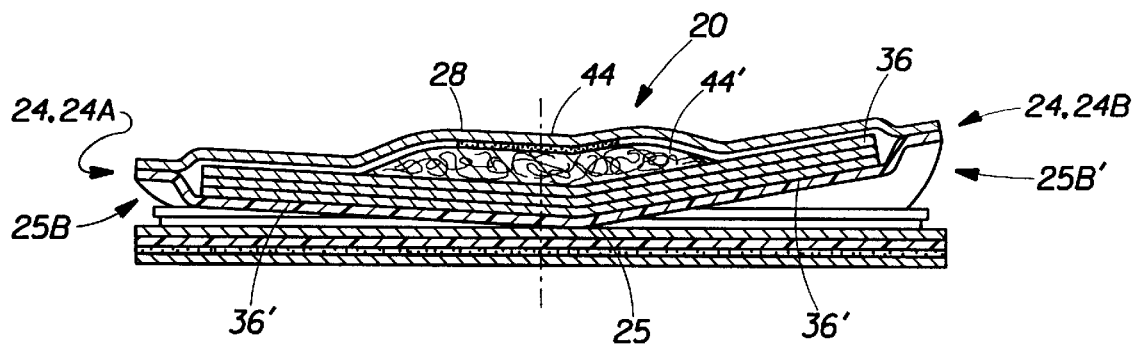
FIG. 12 is a sectional view of an alternate embodiment sanitary napkin taken at an angle similar to that of FIG. 3 in which the core is attached to the backsheet at a transverse juncture located between the end edges of the sanitary napkin.

In alternative embodiments, the transverse juncture 25 may be located at some point between the end edges of the sanitary napkin. FIG. 12 shows that the transverse juncture 25 need not be coincident with an end 24 of the sanitary napkin 20. The sanitary napkin shown in FIG. 12 has two unattached end edges, 25B and 25B'. Preferably, the transverse juncture 25 is longitudinally positioned so that the decoupling of the core 36 from the backsheet 30 will conform the sanitary napkin 20 the wearer's anatomy. Thus, the transverse juncture 25 should be located so that topsheet 28 and core 36 may lift and conform with the wearer's labial tissue in the front portion of the sanitary napkin 20 to more readily intercept menses upon discharge, and in the rear portion of the sanitary napkin 20 will lift to fit into the crevice between the wearer's buttocks (i.e., the "gluteal groove"). In lieu of the transverse juncture 25, the opposed forces of the body and undergarment against the sanitary napkin 20 can hold the core against the backsheet along a transverse line.

The sanitary napkin 20 in such embodiments preferably has a means for controlling the separation of the core 36 from the backsheet 30. The means for controlling the separation of the core 36 from the backsheet 30 prevents the sanitary napkin 20 from unintended gross deformations and from exceeding the desired open position.

The means for controlling the separation of the core from the backsheet used in the sanitary napkin 20 shown in FIGS. 1–5 is a material having a longitudinally-oriented pleat (a "pleated material") 62 that joins the core 36 directly or indirectly to the backsheet 30. The pleated material 62 is provided with longitudinally oriented fold lines 64.

This preferred longitudinally oriented pleated material 62 is provided by an extension of one or more components such as the topsheet 28. As shown in FIG. 2, the topsheet 28 is in a C-folded configuration. The longitudinal ends 28E of the sheet that comprises the topsheet 28 are folded under the central portion of the sheet comprising the topsheet 28 so they are laterally inboard of the longitudinal edges 36C of the absorbent core 36. The longitudinal ends 28E of the sheet are joined to the backsheet 30. The core 36 is able to separate from the backsheet 30 until the pleated material 62 completely unfolds.

Figure 11:
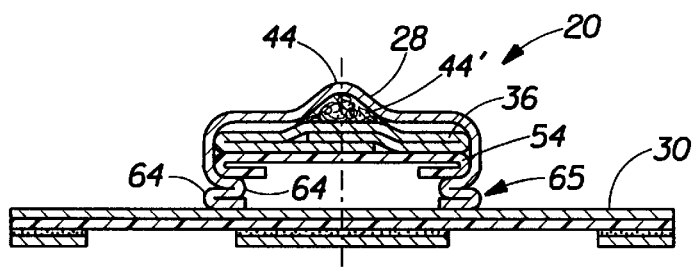
FIG. 11 is a sectional view of an alternate embodiment sanitary napkin taken at an angle similar to that of FIG. 2 in which longitudinally disposed accordion style pleats control the amount of separation of the core from the backsheet.
Figure 13:
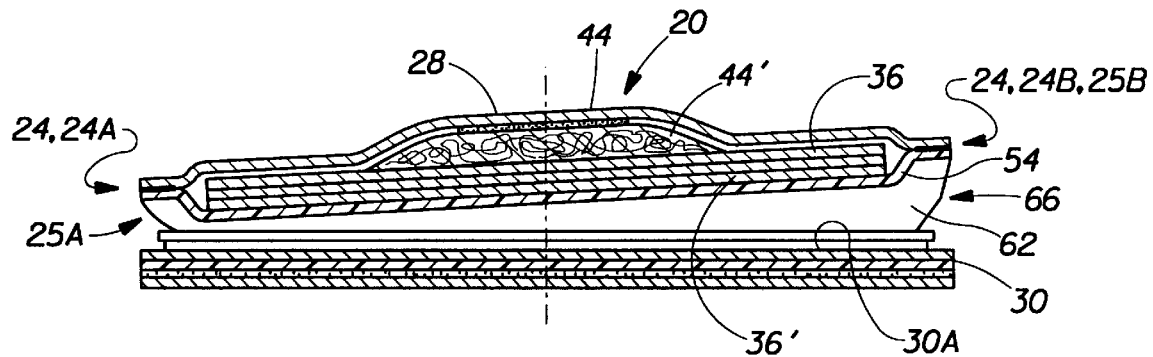
FIG. 13 is a sectional view of an alternate embodiment sanitary napkin taken at an angle similar to that of FIG. 3 in which the core is attached to the backsheet at a transverse juncture located at one end edge of the sanitary napkin and the opposing end edge of the core is attached to the backsheet by a material for controlling the separation therebetween.
Figure 14:
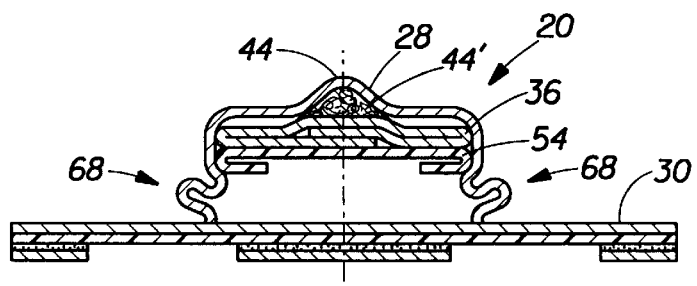
FIG. 14 is a sectional view of an alternate embodiment sanitary napkin taken at an angle similar to that of FIG. 2 in which the amount of separation of the core form the backsheet is controlled by a flaccid material.

Various alternative means for controlling the amount of separation of the core 36 from the backsheet 30 are shown in FIGS. 11, 13, and 14.

FIG. 11 shows an embodiment that employs a material 65 having accordion style longitudinally oriented pleats with a plurality of longitudinally oriented fold lines 64. An accordian pleat provides the advantage that relatively large Z-direction separation is feasible, without requiring the pleated section of the material 65 to have an excessive lateral width.

A sanitary napkin 20 according to the present invention may (as shown in FIG. 13) further comprise a transversely-oriented, preferably liquid impervious, material 66 having a transverse pleat that connects the core 36 and the backsheet 30 at the unattached end edge 25B. The material having the transverse pleat provides the advantage that any menses which exceed the absorbent capacity of the core 36 or which migrate longitudinally toward the unattached end edge 25B of the napkin will be retained in the sanitary napkin 20.

In a less elegant embodiment shown in FIG. 14, the means for controlling the separation of the core 36 from the backsheet 30 of the sanitary napkin 20 may simply comprise flaccid material 68 joining the core 36 to the backsheet 30.

The unattached end edges of the core, such as 36D', in all of the embodiments described in this section may separate in any of those amounts specified in U.S. Pat. No. 5,007,906. The amount of separation of the unattached end edges 36D' and 30D' of the core 36 and backsheet 30 may be measured by either of methods set out in the aforementioned PCT International Patent Application Publication No. WO 92/07535 published in the name of Visscher, et al.

C. Embodiments Having Fasteners Configured to Allow Portions of the Sanitary Napkin Containing the Hump to Separate From the Wearer's Undergarment FIG. 15 shows an embodiment in which the entire central region 76 of the sanitary napkin 20 containing the hump 44 is provided with the ability to separate (or "decouple") from the wearer's panties. This provides the hump 44 with the ability to move into close contact with the wearer's labia when the wearer's panties move in a direction away from the labia during wear.

In the embodiment shown in FIG. 14, this is achieved by providing the sanitary napkin 20 with a particular panty fastener configuration. The sanitary napkin is provided with panty fasteners in the end regions 72 and 74. The sanitary napkin 20, however, is not provided with panty fasteners in the central region 76. This allows the central region 76 containing the hump 44 to decouple from the wearer's panties and move toward the wearer's labia. This provides for more sustained contact of the hump 44 with the wearer's body when the sanitary napkin 20 is worn.

The fastener comprises an adhesive 58 arranged in the form of four generally rectangular strips or patches of adhesive. These patches are arranged so that the overall adhesive pattern resembles a letter "X" with the center of the "X" missing and each of the patches running in a direction from the intersection of the principal longitudinal and transverse centerlines, C, to one of the corners 31 of the sanitary napkin. The ends of the adhesive patches are preferably located as close as possible to the transverse end edges 24 of the sanitary napkin 20. This principle of adhesive configuration is discussed in PCT International patent Publication No. WO 92/04000 entitled "Shape and Adhesive Fastening Means for an Absorbent Article" published in the name of Papa, et al. on Mar. 19, 1992. Other aspects (no adhesive in the central region 76) operate on principles peculiar to the configuration of the sanitary napkin of the present invention.

The adhesive pattern shown in FIG. 15 can also be used on sanitary napkins which have the other types of decoupling features described herein. Other suitable adhesive configurations are also possible. For example, the adhesive could be applied in an inverted V-shape, or chevron pattern, in each end region 72 and 74 of the sanitary napkin 20.

In still other embodiments, any other of the other types of fasteners described above can be used instead of, or in addition to adhesives.

D. Embodiments Having Segmented Cores

In another embodiment of the present invention, the sanitary napkin 20 may have a segmented core and/or hump (or hump-forming element) that is adapted to better conform to the body of the wearer.

The concept of segmented cores in general is described in greater detail in PCT International Patent Application Publication No. WO 92/10984 entitled "Sanitary Napkin Having Transversely Segmented Core" published in the name of Thomas W. Osborn on Jul. 9, 1992.

The core 36 and/or the hump (or hump-forming element) in these embodiments may be divided into a plurality of independent segments, 36*n*. (The letter "n" is an integer which represents the number of independent segments.) More specifically, the segments 36*n* are transversely independently segmented. A core is considered to be transversely segmented when the division line between adjacent segments 36*n* has a vector component within the plane of the core 36 that is generally orthogonal to the principal longitudinal centerline $L_1$. The segments 36*n* are considered to be "independent", as that term is used herein, if the segments 36*n* may move relative to each other, in the Z-direction, without being constrained from such movement by an adjacent segment. For the purposes of the present invention, cores having fold lines and score lines are not considered to have segments which are "independent" because constraint to movement in the Z-direction occurs across the fold line or the score line (even though the fold line or score line may act as a hinge to allow bending of the core at a particular juncture).

(In the discussion that follows, the segmentation will be discussed primarily with respect to that of the core for simplicity of discussion.) It should be understood that the hump or hump-forming element may also be segmented. Alternatively, the hump-forming element may be segmented and the core or the remainder of the core, may not be segmented. The following description of the segments of the core applies to these other structures as well.

The core 36 may be divided into any number of independent segments 36*n*, i.e., a plurality of segments 36*n*. Preferably, the core 36 is divided into three independent segments $36_1$, $36_2$, and $36_3$. A three segment core 36 is desirable because the body of the wearer may be thought of as being divided into three anatomically distinct shaped regions when the wearer is viewed along the principal longitudinal centerline. From the front of the wearer's body to the back of the wearer's body, the first of the three regions may be thought of as the mons region. The mons region has a compound curved convex upward shape when viewed from the front. The second region is defined by the labia majora and has a W-shaped outline when viewed from the front. The third region is determined by the gluteal groove and when viewed from the rear is generally cusp-shaped and defined by two convex upward and outwardly diverging lines. This embodiment of the sanitary napkin 20 is intended to adapt to these three very distinct shapes of the wearer's body.

The sanitary napkin 20 may have a core 36 comprising three disconnected segments $36_1$, $36_2$, and $36_3$. The segments 36n of the core 36 are considered to be "disconnected" if the respective segments 36n are not directly joined to the adjacent segments 36n. The segments 36n may not be directly connected and considered independent when they are indirectly connected, such as through the topsheet 28, backsheet 30, or any tissue wrapping the core 36.

If the sanitary napkin 20 is provided with several segments, such as three segments 36, $36_2$ and $36_3$, they need not be of equal length in the longitudinal direction. For example, a sanitary napkin 20 having three segments with the back segment $36_3$ being about 7.0 centimeters (2.75 inches) in longitudinal direction, the center segment $36_2$ being about 7.0 centimeters (2.75 inches), and the front segment $36_1$ being about 6.4 centimeters (2.5 inches) in longitudinal dimension has been found to work well.

The differences in longitudinal dimension between the segments 36n may be accounted for because the central segment $36_2$ which fits the labia majora region of the wearer's body is the most critical to obtain good fit. The second most critical area to obtain good fit occurs in the back portion of the sanitary napkin 20 so that the gluteal groove (space between the wearer's buttocks) is accommodated. The fit of the front of the sanitary napkin 20 to the mons region of the wearer's body is typically least critical.

Figure 17:
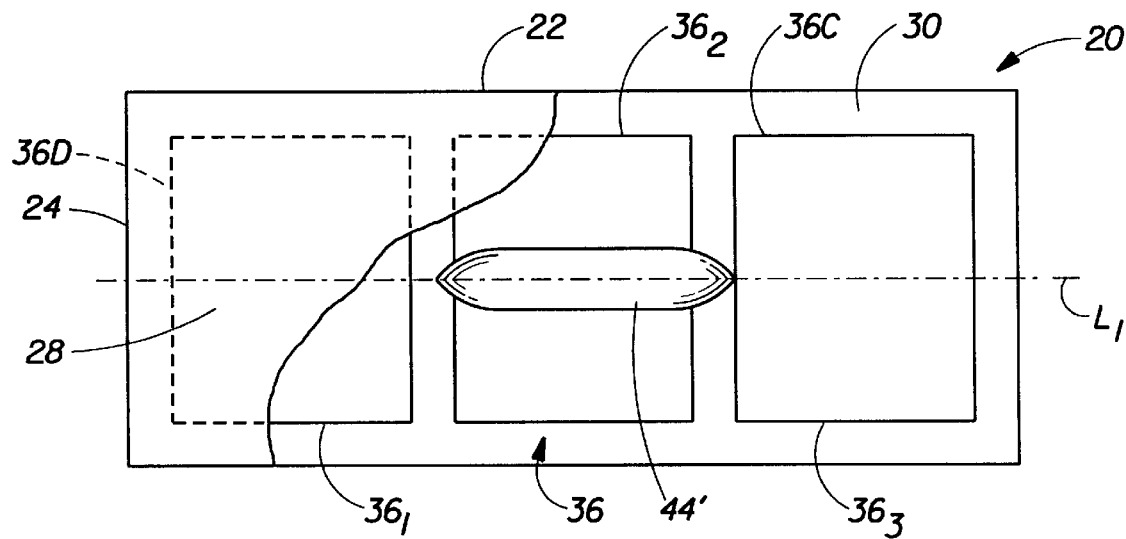
FIG. 17 is a simplified plan view of an alternative embodiment of the sanitary napkin of the present invention shown with the topsheet partially cut away, and having three independent, disconnected, transversely segmented core segments.
Figure 18:
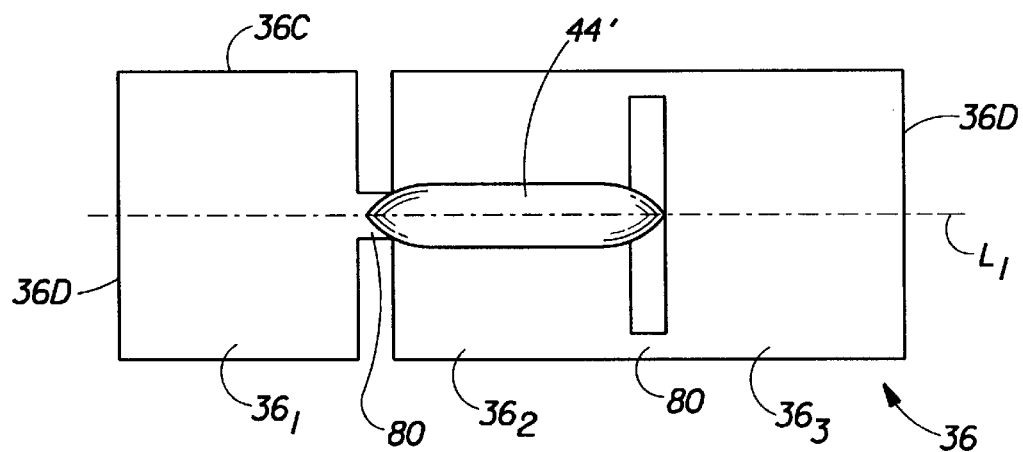
FIG. 18 is a plan view of a variation of the sanitary napkin shown in FIG. 17 which has three independent segments, two segments being joined by isthmic connections registered with the longitudinal edges of the core and two segments joined by an isthmic connection registered with the principal longitudinal centerline of the sanitary napkin.

The segments of the sanitary napkin can, as shown in FIGS. 17 and 18, comprise a hump forming element 44'. The hump-forming element 44' can be segmented or unsegmented. If the hump-forming element 44' is unsegmented, it is preferably registered with one of the segments of the core such as the center segment $36_2$. If it is segmented, the hump-forming element 44' can be divided into two or more (e.g. three) segments. This will typically occur when a relatively long hump-forming element is used. Preferably, if there are three segments, the hump-forming element 44' is registered with the center and back segments $36_2$ and $36_3$ so the portion of the hump registered with the center segment will fit into the space between the wearer's labia and the portion of the hump registered with the back segment will fit into the wearer's gluteal groove.

Referring to FIG. 18, the core 36 of the sanitary napkin 20 may in an alternative embodiment, have independent but connected segments 36n. The segments 36n may be connected through an isthmic connection 80 (that is, connection that resembles a relatively narrow strip connecting two larger areas, an isthmus). The isthmic connection 80 preferably comprises not more than about twenty percent, and preferably not more than about ten percent of the width of the core 36 of the sanitary napkin 20. As illustrated in FIG. 18, the isthmic connection 80 may be disposed along the longitudinal edges 36C of the core 36 of the sanitary napkin 20. Such an arrangement provides maximum relative Z-direction displacement between adjacent segments 36n of the core 36 along the principal longitudinal centerline $L_1$ of the sanitary napkin 20. This arrangement is, therefore, particularly desirable for obtaining good conformance of the core 36 of the sanitary napkin 20 to the vaginal opening of the wearer.

Alternatively, the isthmic connection 80 may be substantially registered with the principal longitudinal centerline $L_1$ of the sanitary napkin 20. This arrangement provides the advantages that the longitudinal edges 36C of the core 36 of the sanitary napkin 20 are free and maximum Z-direction relative displacement between adjacent segments 36n of the core 36 of the sanitary napkin 20 can occur at such longitudinal edges 36C. However, while this arrangement may provide a more comfortable fit to the wearer, with less chafing against the inner thighs, maximum fit with the vaginal opening may not be obtained.

FIG. 18 shows a hybrid sanitary napkin 20 may be made by incorporating both types of isthmic connections 80 described above. Such a sanitary napkin 20 has an isthmic connection 80, registered with the principal longitudinal centerline $L_1$ which joins the front and center segments. This isthmic connection 80 allows the segment of the core 36 registered with the more gradual convex upwardly curved shape of the mons region to have a greater radius of curvature than the segment of the core 36 registered with the sharper, more concave shape of the labia majora region of the wearer's body (which has a lesser radius of curvature.)

The isthmic connections 80 joining the rear and center segments 36n of the sanitary napkin 20 are substantially registered with the longitudinal edges 36C of the core 36 of the sanitary napkin 20. This arrangement allows maximum Z-direction displacement of the rear section to occur at the principal longitudinal centerline $L_1$ of the sanitary napkin 20, so that the rear segment 36n may accurately and comfortably fit into the gluteal groove of the wearer.

E. Other Alternative Embodiments

Several alternative embodiments of sanitary napkins which can be provided with the central absorbent hump of the present invention are shown and described in a number of references. These references include, but are not limited to: U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, and U.S. Pat. No. 4,285,343, entitled "Sanitary Napkin", which issued to McNair on Aug. 25, 1981, the aforementioned U.S. Pat. Nos. 4,950,264 and 5,009,653 both entitled "Thin, Flexible Sanitary Napkin", issued to Osborn on Aug. 21, 1990 and Apr. 23, 1991, respectively, and in U.S. patent application Ser. No. 07/874,872 entitled "Generally Thin, Flexible Sanitary Napkin With Stiffened Center" filed in the name of Osborn on Apr. 28, 1992; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 5,171,302 issued to Buell on Dec. 15, 1992; and U.S. patent application Ser. No. 07/957,575 filed in the name of Cree, et al. on Oct. 7, 1992.

Figure 16:
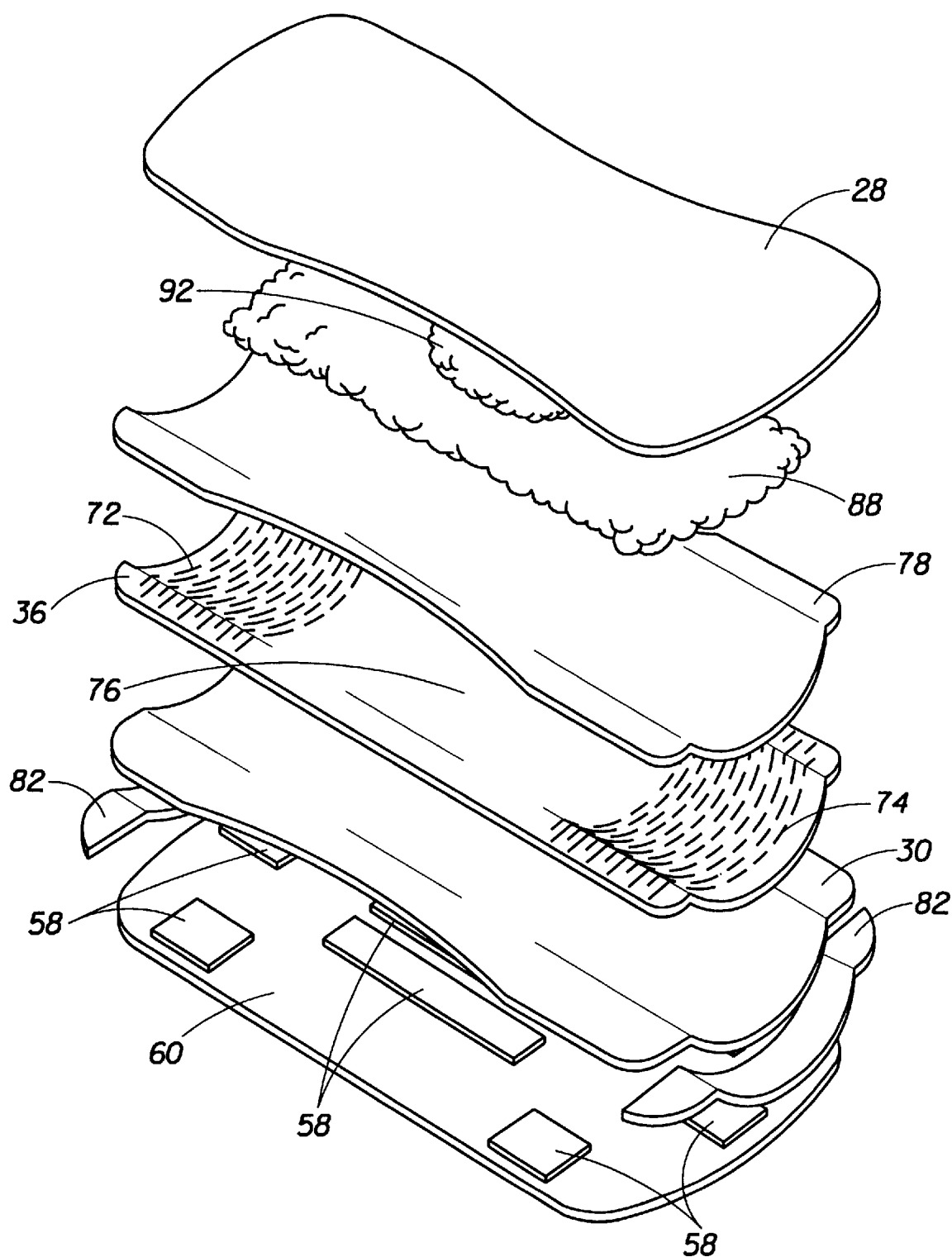
FIG. 16 is an exploded perspective view showing the assembly of an extensible sanitary napkin according to the present invention.

In other embodiments such as shown in FIG. 16, the sanitary napkin 20 may be comprised of components that are extensible (particularly in the longitudinal direction) when the sanitary napkin is worn. As shown in FIG. 16, such a sanitary napkin may comprise: a ringrolled topsheet 28; an extensible adhesive film backsheet; an absorbent core 36 that is slit at the end regions 72 and 74 but not at the central region 76; a layer of capillary channel fibers 88 that is gathered at the center into a tuft 92; a creped paper towel layer 78; and polyethylene end guards 82. The extensible embodiments of the sanitary napkin can be provided with a hump-forming element that may either be extensible or inextensible. Preferably, the sanitary napkin 20 is capable of elongating between about 15% and about 40% of its unstretched length. This extensibility provides better in-use fit, comfort, and decreased staining.

Such embodiments are described in the following patent applications which were filed Jul. 23, 1991 (of which the present application is a continuation-in-part): U.S. patent application Ser. No. 07/734,404 filed in the names of Thompson, et al.; U.S. patent application Ser. No. 07/734,392 filed in the names of Thompson, et al.; and, U.S. patent application Ser. No. 07/734,405 filed in the names of Buenger, et al. These patent applications may be referred to collectively as the "Capillary Channel Fiber" patent applications. Additional extensible sanitary napkin embodiments are described in U.S. patent application Ser. No. 07/915,133 and U.S. patent application Ser. No. 07/915,284 both filed in the name of Osborn, et al. on Jul. 23, 1992. These latter two patent applications may be referred to collectively as the "Stretchable Absorbent Article" patent applications.

In other embodiments, the sanitary napkin may be provided with a curved shape. Such embodiments are described in the following patent applications filed Jul. 23, 1992: U.S. patent application Ser. No. 07/915,285 filed in the name of Johnson, et al. (P&G Case 4674); U.S. patent application Ser. No. 07/915,202 filed in the name of Osborn, et al. (P&G Case 4675); U.S. patent application Ser. No. 07/915,201 filed in the name of Olsen, et al.; and U.S. patent application Ser. No. 07/915,134 filed in the name of Hines, et al. (P&G Case 4677).

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

It is to be understood that all of the limits and ranges specified in the foregoing description of the sanitary napkin include narrower ranges and limits that are within the specified limits and ranges. Thus, for example if a range, such as the length of the hump, is specified as being between about 1.5 inches and about 4 inches, all narrower ranges (such as between about 2 inches and about 3 inches, etc.) may be claimed even though these ranges are not separately listed.

While particular embodiments of the present invention have been illustrated and described, it would be obvious to those skilled in the art that various other changes and modifications can be made without departing from the spirit and scope of the invention. It is therefore intended to cover in the appended Claims all such changes and modifications that are within the scope of this invention.

What is claimed is:

1. An extensible sanitary napkin having a principal longitudinal centerline, a principal transverse centerline, a body surface, a garment surface, a longitudinal central region disposed along the length of at least a portion of said principal longitudinal centerline, and longitudinal side regions that lie transversely outboard of said longitudinal central region, said longitudinal side regions having a caliper of less than or equal to about 5 millimeters, said sanitary napkin comprising:
    an extensible liquid pervious topsheet;
    an extensible liquid impervious backsheet joined to said topsheet;
    an absorbent material positioned between said topsheet and said backsheet; and
    a longitudinal medial hump on said body surface in said longitudinal central region of said sanitary napkin, said hump having a point of maximum amplitude and a caliper measured at its point of maximum amplitude that is greater than about 3 millimeters and at least about 2.0 times the caliper of said portions of said longitudinal side regions.

2. The extensible sanitary napkin of claim 1 wherein said hump is at least partially formed by a hump-forming element.

3. The extensible sanitary napkin of claim 2 wherein said hump-forming element is also extensible.

4. The extensible sanitary napkin of claim 1 wherein the caliper at said point of maximum amplitude is between about 4 mm. and about 15 mm.

5. The sanitary napkin of claim 4 wherein said portions of said surrounding regions have a caliper of less than or equal to about 4 mm.

6. An extensible sanitary napkin having a principal longitudinal centerline, a principal transverse centerline, a body surface, a garment surface, a longitudinal central region disposed along the length of at least a portion of said principal longitudinal centerline, surrounding absorbent regions located outboard of said longitudinal central region, at least some portions of said surrounding regions having a caliper of less than or equal to about 5 millimeters, said sanitary napkin comprising:
    an extensible liquid pervious topsheet;
    an extensible liquid impervious backsheet joined to said topsheet;
    an absorbent material positioned between said topsheet and said backsheet; and
    a longitudinal medial hump on said body surface in said longitudinal central region of said sanitary napkin, said hump having a point of maximum amplitude and a caliper measured at its point of maximum amplitude that is greater than about 3 millimeters and at least about 2.0 times the caliper of said portions of said surrounding regions
    wherein said longitudinal central region has a flexure-resistance that is greater than the flexure-resistance of said portions of said surrounding regions, and the flexure-resistance of said longitudinal central region is up to about 1,000 grams, and the flexure-resistance of said portions of said surrounding regions is less than or equal to about 700 grams.

7. The extensible sanitary napkin of claim 6 wherein the caliper at said point of maximum amplitude is between about 4 mm and about 15 mm.

8. The sanitary napkin of claim 7 wherein said portions of said surrounding regions have a caliper of less than or equal to about 4 mm.

9. A sanitary napkin having a principal longitudinal centerline, a transverse centerline, a body surface, a garment surface, a longitudinal central region disposed along the length of at least a portion of said principal longitudinal centerline, and surrounding regions at least laterally outboard of said longitudinal central region, said sanitary napkin comprising:
    a liquid pervious topsheet;
    a liquid impervious backsheet joined to said topsheet;
    an absorbent core positioned between said topsheet and said backsheet;
    a longitudinal medial hump on said body surface in said longitudinal central region of said sanitary napkin;

said core being joined to said backsheet along at least two longitudinal junctures, the remainder of said core, including at least one end edge being unattached to said backsheet so that said unattached portion of said core may move apart and separate from said backsheet.

10. The sanitary napkin of claim 9 further comprising a means for controlling the separation of said core from said backsheet.

* * * * *